United States Patent
Koshijima et al.

(10) Patent No.: US 10,786,398 B2
(45) Date of Patent: *Sep. 29, 2020

(54) PRODUCTION DEVICE AND PRODUCTION METHOD FOR COMPOSITE STRETCHABLE MEMBER

(71) Applicant: ZUIKO CORPORATION, Osaka (JP)

(72) Inventors: Miwa Koshijima, Osaka (JP); Hideyuki Nakamura, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 204 days.

This patent is subject to a terminal disclaimer.

(21) Appl. No.: 15/736,429

(22) PCT Filed: Jun. 17, 2016

(86) PCT No.: PCT/JP2016/068058
§ 371 (c)(1),
(2) Date: Dec. 14, 2017

(87) PCT Pub. No.: WO2016/208502
PCT Pub. Date: Dec. 29, 2016

(65) Prior Publication Data
US 2018/0147095 A1 May 31, 2018

(30) Foreign Application Priority Data
Jun. 22, 2015 (JP) .................. 2015-124928

(51) Int. Cl.
*A61F 13/15* (2006.01)
*B32B 37/06* (2006.01)
(Continued)

(52) U.S. Cl.
CPC .. *A61F 13/15585* (2013.01); *A61F 13/15593* (2013.01); *A61F 13/15699* (2013.01);
(Continued)

(58) Field of Classification Search
CPC ........ A61F 13/4902; A61F 2013/15878; A61F 13/15585; A61F 13/15699;
(Continued)

(56) References Cited

U.S. PATENT DOCUMENTS 5,525,175 A * 6/1996 Blenke .............. A61F 13/15593
156/161
6,291,039 B1 9/2001 Combe
(Continued)

FOREIGN PATENT DOCUMENTS

CN 103300972 9/2013
EP 1 666 178 6/2006
(Continued)

OTHER PUBLICATIONS

Extended European Search Report dated Feb. 28, 2018 in European Application No. 16814273.5.
(Continued)

*Primary Examiner* — John L Goff, II
(74) *Attorney, Agent, or Firm* — Wenderoth, Lind & Ponack, L.L.P.

(57) ABSTRACT

Using a conveyance roller having an outer peripheral surface which is capable of conveying two sheets with an elastic element sandwiched therebetween, in a longitudinal direction of the sheets, and formed with a convex section; and a clamping and pressing device, the sheets with the elastic element sandwiched therebetween are ultrasonic-welded together under pressing. The convex section is formed in a shape extending along a line intersecting a conveyance direction of the conveyance roller, and the convex section is provided with a plurality of grooves at positions spaced apart from each other in a longitudinal direction thereof, wherein each of the grooves extends in the conveyance direction of the conveyance roller to allow a portion of the
(Continued)

sheets on which the elastic element is disposed, to be inserted therein.

16 Claims, 21 Drawing Sheets

(51) Int. Cl.
| | |
|---|---|
| *B32B 5/02* | (2006.01) |
| *A61F 13/49* | (2006.01) |
| *B29C 65/08* | (2006.01) |
| *B29C 65/00* | (2006.01) |
| *B32B 25/04* | (2006.01) |
| *B32B 37/00* | (2006.01) |
| *B29K 621/00* | (2006.01) |
| *B29L 31/48* | (2006.01) |

(52) U.S. Cl.
CPC .... *A61F 13/15739* (2013.01); *A61F 13/4902* (2013.01); *A61F 13/49011* (2013.01); *B29C 65/08* (2013.01); *B29C 65/086* (2013.01); *B29C 66/1122* (2013.01); *B29C 66/43* (2013.01); *B29C 66/7294* (2013.01); *B29C 66/8145* (2013.01); *B29C 66/81433* (2013.01); *B29C 66/83411* (2013.01); *B32B 5/02* (2013.01); *B32B 25/04* (2013.01); *B32B 37/0084* (2013.01); *B32B 37/06* (2013.01); *A61F 2013/15878* (2013.01); *B29C 66/221* (2013.01); *B29C 66/234* (2013.01); *B29C 66/431* (2013.01); *B29C 66/433* (2013.01); *B29C 66/71* (2013.01); *B29K 2621/00* (2013.01); *B29K 2995/0046* (2013.01); *B29L 2031/4878* (2013.01); *B32B 2307/51* (2013.01); *B32B 2319/00* (2013.01); *B32B 2555/02* (2013.01)

(58) Field of Classification Search
CPC .......... A61F 13/15739; A61F 13/15593; A61F 13/15601; A61F 13/15609; A61F 13/49011; A61F 13/49012; A61F 13/49014; A61F 13/49015; A61F 13/49017; A61F 13/49019; A61F 13/51464; A61F 2013/15861; A61F 2013/15869; A61F 2013/49025; A61F 2013/49026; A61F 2013/49028; B29C 65/08; B29C 65/083; B29C 65/084; B29C 65/085; B29C 65/086; B29C 65/088; B29C 66/43; B29C 65/081; B29C 65/082; B29C 65/087; B29C 66/433; B29C 66/81427; B29C 66/81431; B29C 66/81433; B29C 66/81435; B29C 66/81463; B29C 66/81465; B29C 66/81467; B29C 66/81469; B29C 66/8432; B29C 66/344; B29C 66/81429; B32B 37/0084
See application file for complete search history.

(56) References Cited

U.S. PATENT DOCUMENTS

| | | | |
|---|---|---|---|
| 2002/0046802 A1* | 4/2002 | Tachibana | A61F 13/15593 156/209 |
| 2003/0144643 A1 | 7/2003 | Jarpenberg et al. | |
| 2004/0127881 A1* | 7/2004 | Stevens | A61F 13/15203 604/385.22 |
| 2004/0133180 A1 | 7/2004 | Mori et al. | |
| 2006/0270302 A1 | 11/2006 | Ando et al. | |
| 2013/0233472 A1 | 9/2013 | Fort | |
| 2014/0196836 A1 | 7/2014 | Fort | |

FOREIGN PATENT DOCUMENTS

| | | |
|---|---|---|
| JP | 2002-273808 | 9/2002 |
| JP | 2005-212405 | 8/2005 |
| JP | 2008-55198 | 3/2008 |
| JP | 2009-56156 | 3/2009 |
| JP | 2009-241607 | 10/2009 |
| JP | 2012-239531 | 12/2012 |
| JP | 2014-275 | 1/2014 |
| WO | 03/059603 | 7/2003 |
| WO | 2014/010340 | 1/2014 |

OTHER PUBLICATIONS

Office Action dated Sep. 5, 2018 in corresponding Japanese Application No. 2017-524849, with English translation.
Chinese Office Action dated Apr. 22, 2019 in Chinese Patent Application No. 2016800352417, with English-language Translation.
International Search Report dated Sep. 13, 2016 in International (PCT) Application No. PCT/JP2016/068058.

* cited by examiner

FIG. 16
STAGE 1
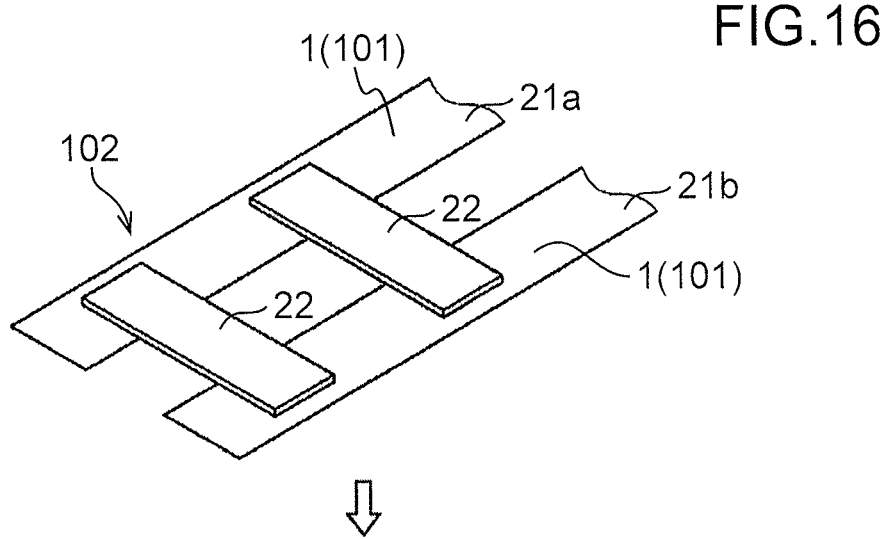
STAGE 2
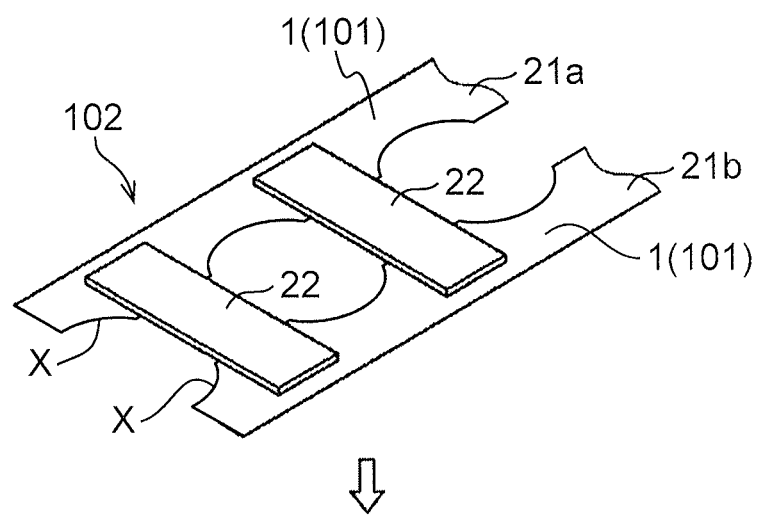
STAGE 3
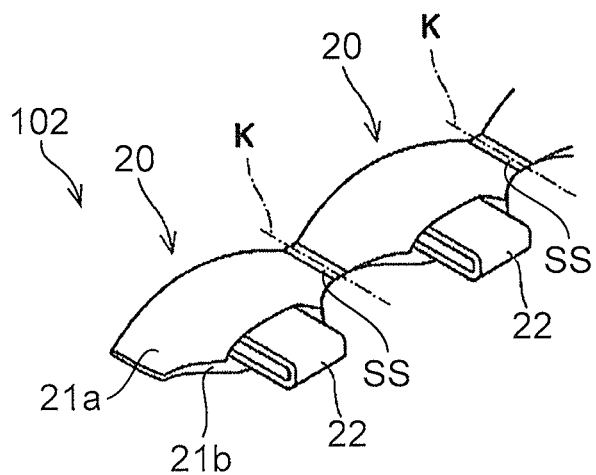

PRODUCTION DEVICE AND PRODUCTION METHOD FOR COMPOSITE STRETCHABLE MEMBER

TECHNICAL FIELD

The present invention relates to an apparatus for producing a composite stretchable member, and a method for the production.

BACKGROUND ART

Heretofore, there has been known a wearable article such as a disposable diaper having a waist portion and a crotch portion. In this type of wearable article such as a disposable diaper, with a view to providing good wearing comfort or the like, the waist portion of the wearable article is composed of a composite stretchable member capable of being stretched and restored, in some cases.

As an apparatus for producing the composite stretchable member, there has been known an apparatus described, for example, in WO 2014/010340 A.

In the apparatus described in WO 2014/010340 A, first of all, a hot-melt material is applied to a surface of a given first sheet. Then, an elastic element is disposed on the surface of the first sheet in a state in which it is stretched in a longitudinal direction of the first sheet. Subsequently, a second sheet is disposed on the surface of the first sheet in a state in which it covers the elastic element. Accordingly, the elastic element is disposed between the sheets. Then, in this state, the sheets are bonded together, and further the elastic element is bonded to the sheets, to thereby produce a composite stretchable member.

In this apparatus, the hot-melt material is used to bond the sheets together and further bond the elastic element to the sheets, so that it is possible to suppress damage to the elastic element during the bonding.

The apparatus described in WO 2014/010340 A needs to prepare the hot-melt material, in addition to the sheets and the elastic element, and to be equipped with a device for applying the hot-melt material to the first sheet. Thus, there is a possibility of causing upsizing/complication of production equipment, and an increase in power consumption.

SUMMARY OF INVENTION

It is an object of the present invention to provide a composite stretchable member production apparatus and method capable of suppressing damage to an elastic element while simplifying production equipment to suppress power consumption.

Solution to Technical Problem

As a means to solve the above problems, the present invention provide a composite stretchable member production apparatus for producing a composite stretchable member comprising two sheets and a plurality of elastic elements sandwiched between the two sheets, by bonding the two sheets together and further bonding each of the elastic elements to the sheets, while conveying the two sheets along a longitudinal direction thereof. The composite stretchable member production apparatus comprises: a bonding device which bonds each of the elastic elements to the sheets and further bonds the sheets together, by means of welding, in a state in which the elastic elements are sandwiched between the two sheets being conveyed; and a guide device which guides, to the bonding device, the two sheets and the elastic elements in such a manner as to enable each of the elastic elements to be sandwiched between the two sheets while extending in the longitudinal direction of the sheets, wherein the bonding device comprises: a conveyance roller having an outer peripheral surface rotatable about a given axis to convey the two sheets with the elastic elements sandwiched therebetween, in the longitudinal direction of the sheets; and a clamping and pressing device which is opposed to the outer peripheral surface of the conveyance roller, and clamps and presses the two sheets with the elastic elements sandwiched therebetween, in cooperation with the outer peripheral surface, wherein the bonding device is configured to apply heat to the sheets between the conveyance roller and the clamping and pressing device, and wherein the outer peripheral surface of the conveyance roller is formed with at least one convex section protruding toward the clamping and pressing device, wherein the convex section has a shape extending along a line intersecting a conveyance direction of the conveyance roller, and has a plurality of grooves lying in spaced-apart relation to each other on the line intersecting the conveyance direction of the conveyance roller and each extending in the conveyance direction of the conveyance roller.

In this apparatus, the sheets and the elastic elements are heated and pressed to weld the sheets together and further weld each of the elastic elements to the sheets, so that, as compared to the case where the bonding is performed using a hot-melt material, it becomes unnecessary to prepare the hot-melt material. Further, it is possible to bond together the two sheets with the elastic elements therebetween, while conveying the two sheets by the conveyance roller, so that, as compared to the case where a device for applying a hot-melt material is provided, it becomes possible to simplify production equipment to suppress power consumption.

On the other hand, in this apparatus, it is necessary to clamp and press the two sheets with the elastic elements sandwiched therebetween, so that there is a possibility that the elastic elements are damaged by the pressing. Considering this, in this apparatus, the convex section formed on the outer peripheral surface of the conveyance roller is formed with the grooves each extending in the conveyance direction of the conveyance roller. Thus, when the sheets are clamped and pressed by the convex section and the clamping and pressing device, the elastic elements are allowed to escape into the grooves. This makes it possible to keep down a pressure to be applied to the elastic elements to thereby suppress damage to the elastic elements.

The present invention also provides a composite stretchable member production method for producing a composite stretchable member using the above composite stretchable member production apparatus. The composite stretchable, member production method comprises: a guiding step of guiding, to the bonding device by the guide device, two sheets and a plurality of elastic elements in such a manner to each of the elastic elements to be sandwiched between the two sheets while extending in a longitudinal direction of the sheets; and a bonding step of clamping and pressing, by the clamping and pressing device and the convex section, the two sheets with the elastic elements sandwiched therebetween, and heating a clamped and pressed part of the two sheets to thereby bond each of the elastic elements to the sheets and further bond the sheets together, by means of welding, wherein the bonding step includes bonding each of the elastic elements to the sheets and further bonding the sheets together, in a state in which each of the elastic elements is disposed on a portion of one of the sheet located on the side of the conveyance roller, and part of the portion of the sheet and at least part of the elastic element are inserted in ones of the grooves of the convex section.

The present invention makes it possible to produce a composite stretchable member while suppressing damage to an elastic element, with a simplified configuration.

BRIEF DESCRIPTION OF DRAWINGS

FIG. 16 is a diagram for explaining a production method for the disposable diaper depicted in FIG. 15.

DESCRIPTION OF EMBODIMENTS

With reference to the accompanying drawings, the present invention will now be described based on embodiments thereof. It should be noted that the following embodiments will be shown and described as specific example of the present invention, but are not meant to limit the technical scope of the present invention set forth in the appended claims.

(1) Configuration of Composite Stretchable Member

Figure 1:
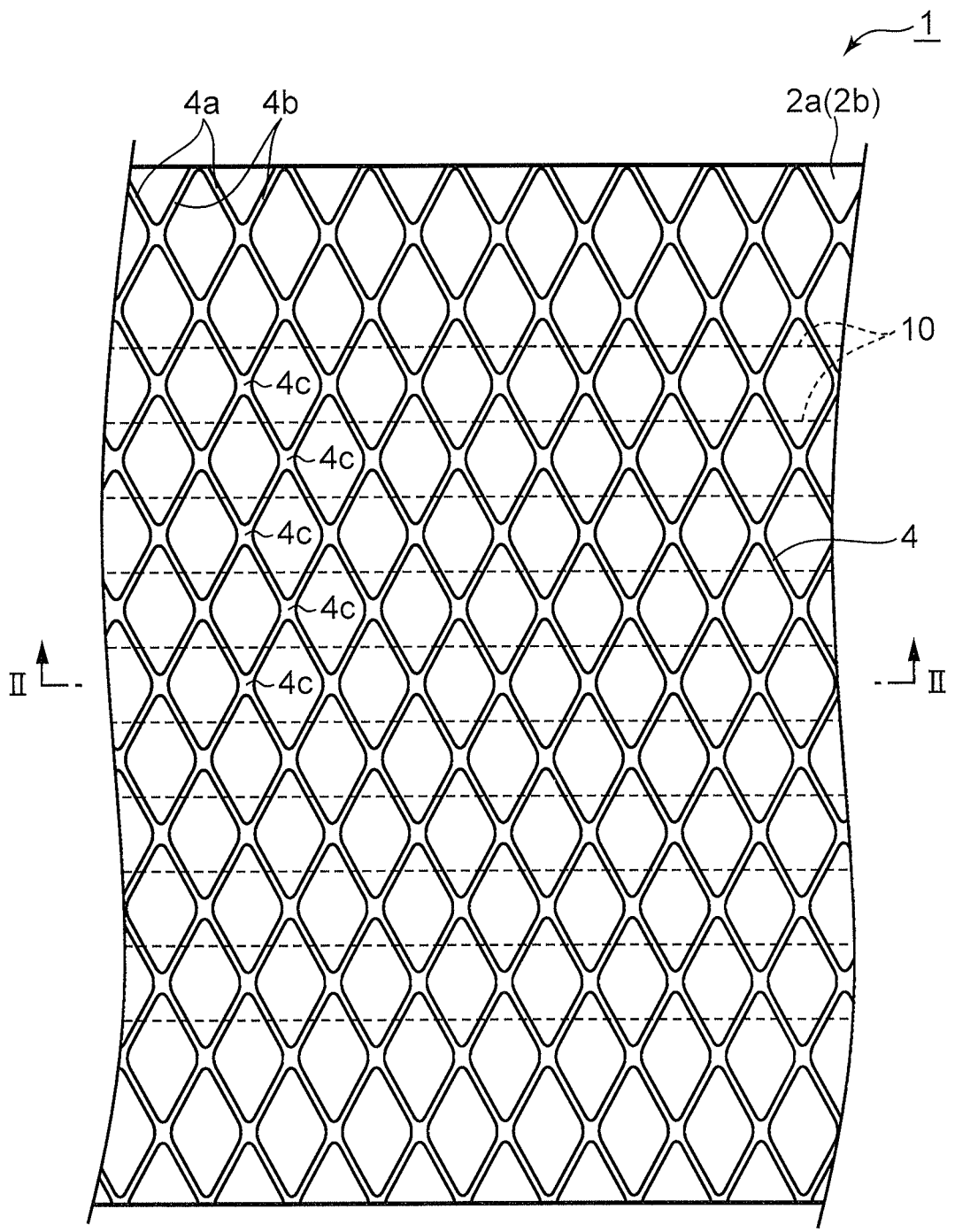
FIG. 1 is a plan view of a composite stretchable member according to one embodiment of the present invention.
Figure 2:
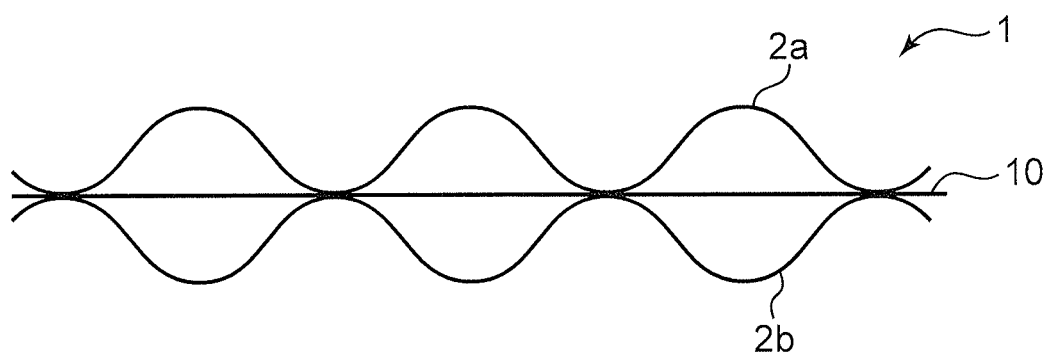
FIG. 2 is part of a sectional view taken along the line II-II in FIG. 1.

FIG. 1 is a plan view of a composite stretchable member according to one embodiment of the present invention. FIG. 2 is part of a sectional view taken along the line II-II in FIG. 1.

The composite stretchable member 1 comprises two long sheets 2a, 2b which are opposed to each other, and a plurality of long elastic elements 10 which are stretchable in a longitudinal direction thereof. Each of the elastic elements 10 is disposed between the two sheets 2a, 2b to extend along the longitudinal direction of the sheets 2a, 2b (a rightward-leftward direction in FIG. 1), in such a manner as to be stretchable in the longitudinal direction, i.e., so as to be stretched and restored in the longitudinal direction. In this embodiment, these elastic elements 10 are arranged at equal intervals (equally spaced-apart relation to each other) in a width direction of the sheets 2a, 2b (a direction orthogonal to the longitudinal direction of the sheets 2a, 2b), to extend parallel to the longitudinal direction of the sheets 2a, 2b.

In this embodiment, non-woven fabric is used as a material for the sheets 2a, 2b.

Figure 3:
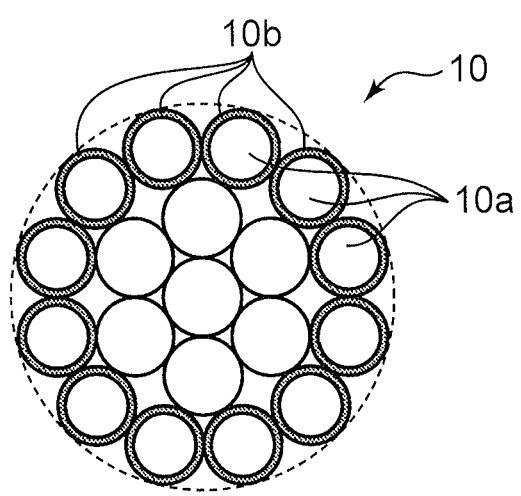
FIG. 3 is a schematic sectional view depicting a cross-section of an elastic element.

In this embodiment, as depicted in FIG. 3, each of the elastic elements 10 is formed using a multi-strand element in which a plurality of rubber strings (fibrous elastic bodies) 10a are assembled in the form of a bundle, wherein each of at least part of the rubber strings 10a has an outer periphery covered by a covering layer 10b. More specifically, among the plurality of rubber strings 10a, each of some rubber strings 10a disposed particularly in an outer periphery of the elastic elements 10 is covered by the covering layer 10b. Alternatively, it is to be understood that each of the plurality of rubber strings 10a may be covered by the covering layer 10b.

Examples of a material for the rubber strings 10a include polyurethane. Examples of a material for the covering layer 10b include lubricant such as silicone oil, or magnesium stearate.

The two sheets 2a, 2b are bonded together, and further the elastic elements 10 is bonded to the sheets 2a, 2b, in lattice-patterned bonding sections 4, as depicted in FIG. 1.

Figure 4:
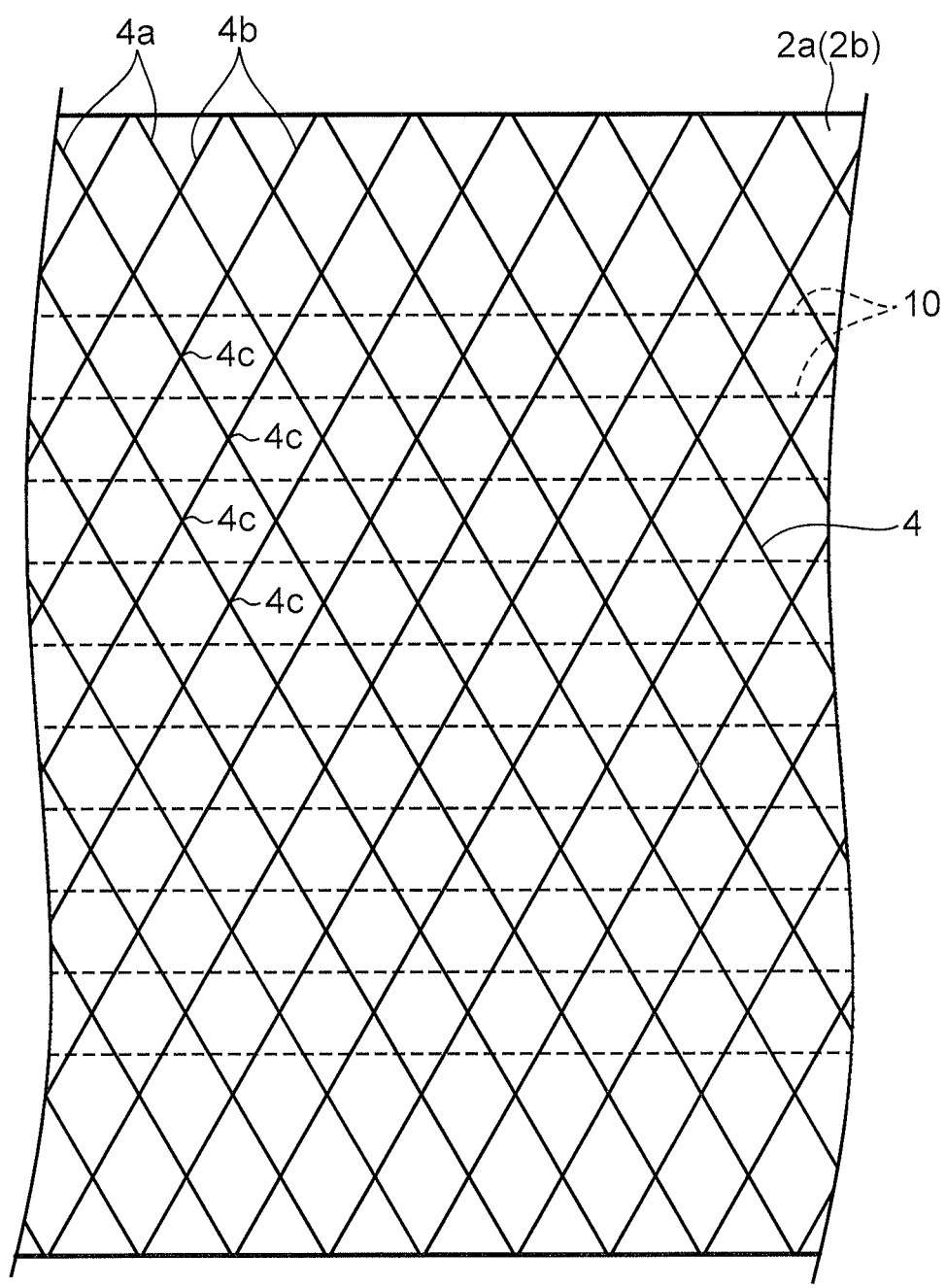
FIG. 4 is a view corresponding to FIG. 1 and schematically depicting bonding sections.

FIG. 4 is a view corresponding to FIG. 1 and schematically depicting the bonding sections. As depicted in FIGS. 1 and 4, the bonding sections 4 comprise a plurality of first bonding sections 4a, and a plurality of second bonding sections 4b.

The first bonding sections 4a are arranged at equal intervals in the longitudinal direction of the sheets 2a, 2b, to extend parallel to each other along the width direction of the sheets 2a, 2b.

The second bonding sections 4b are arranged at equal intervals in the longitudinal direction of the sheets 2a, 2b, to extend parallel to each other along the width direction of the sheets 2a, 2b. The second bonding sections 4b extend to intersect the first bonding sections 4a to thereby form the lattice-patterned bonding sections 4.

In this embodiment, each of the first bonding sections 4a and the second bonding sections 4b is inclined with respect to the width direction of the sheets 2a, 2b. Further, an angle of this inclination is set to be less than 45 degrees. For example, this inclination angle is set to 30 degrees.

Each of the first bonding sections 4a and the second bonding sections 4b has a symmetrical shape with respect to each of two straight lines extending in the longitudinal and width directions of the sheets 2a, 2b. The first bonding sections 4a and the second bonding sections 4b are arranged such that a spaced-apart distance between adjacent ones of the first bonding sections 4a is coincident with a spaced-apart distance between adjacent ones of the second bonding sections 4b. Accordingly, each of the bonding section 4 defines diamond shape whose two diagonal lines extend in the longitudinal and width directions of the sheets 2a, 2b. In particular, as mentioned above, each of the first bonding sections 4a and the second bonding sections 4b is inclined at an inclination angle of less than 45 degrees with respect to the width direction of the sheets 2a, 2b, and therefore each of the diamond shapes is defined to extend in the width direction. Intersection points 4c of the first bonding sections 4a with the second bonding sections 4b (hereinafter referred to occasionally as "bonding section-side intersection points") lie side-by-side at equal intervals on a straight line extending in the longitudinal direction of the sheets 2a, 2b, and also lie side-by-side at equal intervals on a straight line extending in the width direction of the sheets 2a, 2b.

Each of the bonding sections 4 intersects all of the elastic elements 10, and extends along a line intersecting a stretchable direction of the elastic elements 10. Specifically, each of the bonding sections 4 extends over between widthwise opposite regions of the sheets 2a, 2b outside a region in which the elastic elements 10 are arranged.

Each of the elastic elements 10 intersects the bonding sections 4, at positions other than the bonding section-side intersection points 4c, i.e., at positions spaced apart from the bonding section-side intersection points 4c, wherein the elastic element 10 is bonded to the sheets 2a, 2b at these positions.

This will be more specifically described with reference to FIG. 5 enlargedly depicting part of FIG. 1.

Figure 5:
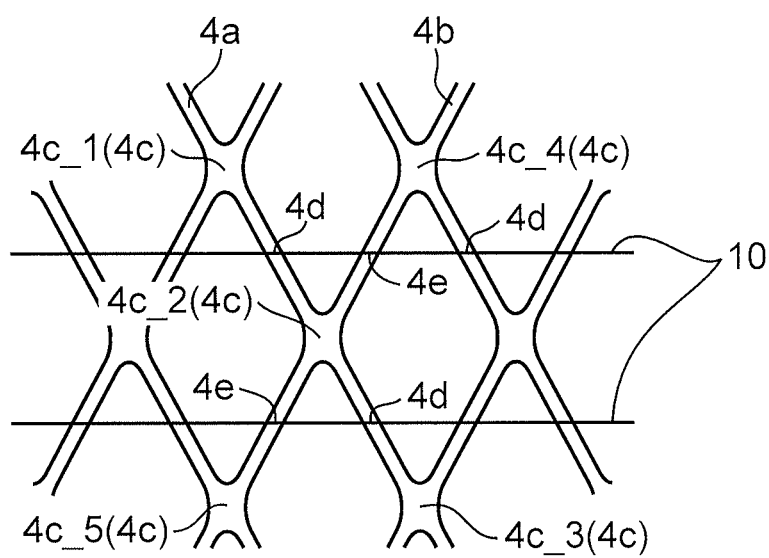
FIG. 5 is a view enlargedly depicting part of FIG. 1.

Each of the elastic elements 10 is disposed to pass, respectively, through positions between adjacent ones of the bonding section-side intersection points 4c on each of the first bonding sections 4a (e.g., pass, respectively, between the bonding section-side intersection point $4c\_1$ and the bonding section-side intersection point $4c\_2$, and between the bonding section-side intersection point $4c\_2$ and the bonding section-side intersection point $4c\_3$, depicted in FIG. 5). That is, a first elastic element-side intersection point 4d which is an intersection point of each of the elastic elements 10 with each of the first bonding sections 4a lies between adjacent ones of the bonding section-side intersection points 4c on the first bonding section 4a, and the elastic element 10 and the sheets 2a, 2b are bonded together at the position of this intersection point 4d.

Similarly, each of the elastic elements 10 is disposed to pass, respectively, through positions between adjacent ones of the bonding section-side intersection points 4c on the second bonding sections 4b (e.g., pass, respectively, between the bonding section-side intersection point $4c\_4$ and the bonding section-side intersection point $4c\_2$, and between the bonding section-side intersection point $4c\_2$ and the bonding section-side intersection point $4c\_5$, depicted in FIG. 5). That is, a second elastic element-side intersection point 4e which is an intersection point of each of the elastic elements 10 with each of the second bonding sections 4b lies between adjacent ones of the bonding section-side intersection points 4c on the second bonding sections 4b, and the elastic element 10 and the sheets 2a, 2b are bonded together at the position of this intersection point 4e.

In this embodiment, each of the elastic elements 10 is disposed to pass through a center between adjacent ones of the bonding section-side intersection points 4c on each of the first bonding sections 4a, and a center between adjacent ones of the bonding section-side intersection points 4c on each of the second bonding sections 4b, i.e., to intersect the first bonding section 4a and the second bonding section 4b at these centers, and bonded to the sheets 2a, 2b at these centers.

Accordingly, the first elastic element-side intersection point 4d and the second elastic element-side intersection point 4e alternately lie in a straight line extending in the width direction of the sheets 2a, 2b. Further, intersection points of the elastic elements 10 with the bonding sections 4, i.e., bonded points 4d, 4e of each of the elastic elements 10 to the sheets 2a, 2b, are arranged at equal intervals in the longitudinal direction of the sheets 2a, 2b.

In the bonding sections 4, the two sheets 2a, 2b are bonded together, and further each of the elastic elements 10 is bonded to the sheets 2a, 2b, by means of welding. In this embodiment, they are bonded together by means of ultrasonic welding.

The sheets 2a, 2b are partially melted, and welded to each other, so that they are bonded together. On the other hand, as to the elastic elements 10 and the sheets 2a, 2b, the part of the sheets 2a, 2b is partially melted, and the covering layers 10b in each of the elastic elements 10 are melted, so that each of the elastic elements 10 is welded to the sheets 2a, 2b.

Specifically, in this embodiment, the rubber strings 10a and the covering layers 10b are formed using rubber strings having a melting point of about 200° C. and magnesium stearate having a melting point of less than about 200° C. (of about 120° C.), respectively. Thus, during welding of each of the elastic elements 10 to the sheets 2a, 2b, the covering layers 10b are melted without causing melting of the rubber strings 10a, and welded to the sheets 2a, 2b.

(2) Production Apparatus for Composite Stretchable Member

Next, a production apparatus for producing the above composite stretchable member 1 will be described.

Figure 6:
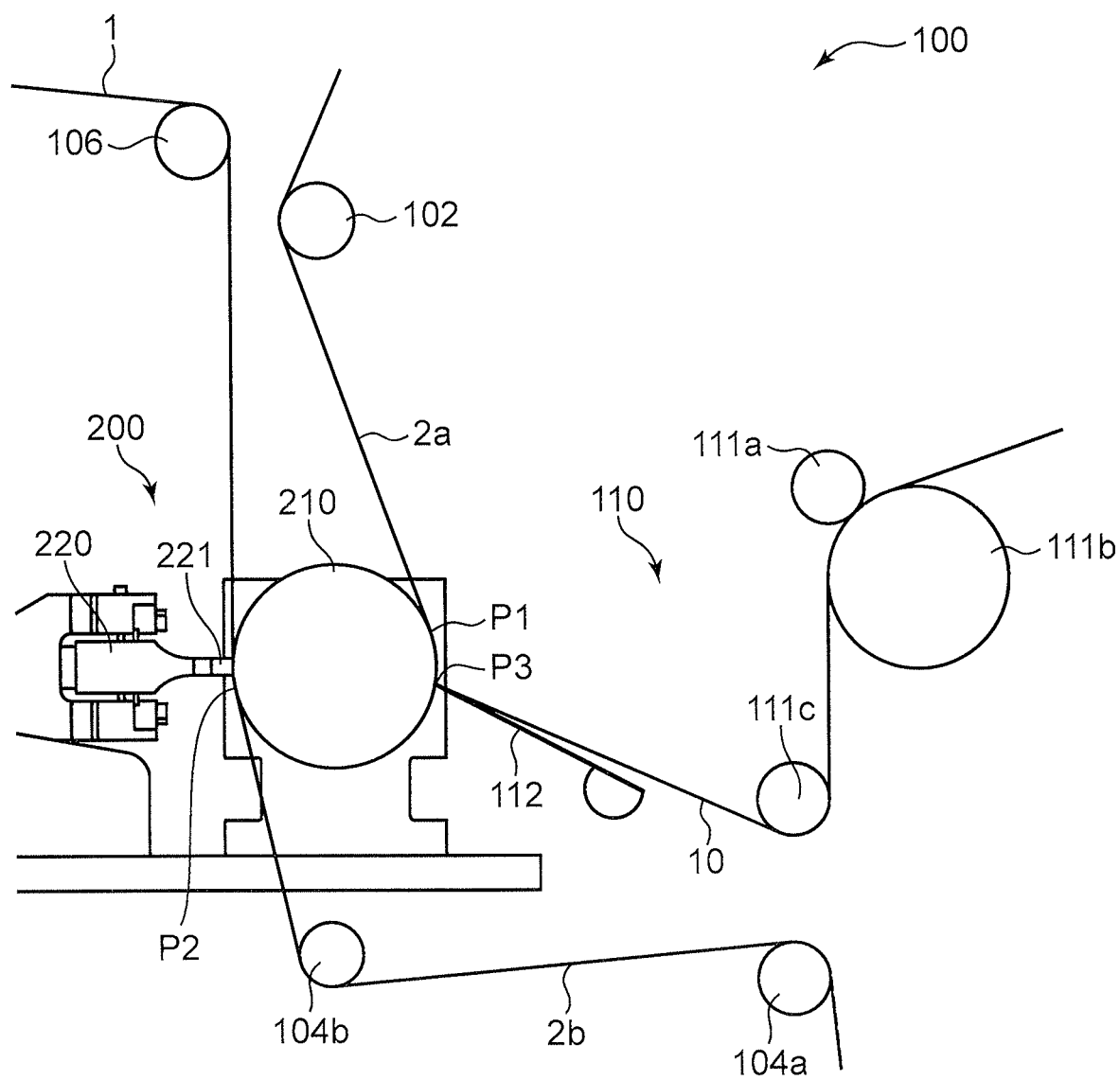
FIG. 6 is a schematic diagram of a production apparatus for the composite stretchable member.

FIG. 6 is a schematic diagram of the production apparatus 100.

The production apparatus 100 comprises: a bonding device 200 for bonding each of the elastic elements 10 to the sheets 2a, 2b and further bonding the sheets 2a, 2b together, by means of ultrasonic welding, in a state in which the elastic elements 10 are sandwiched between the sheets 2a, 2b; a first guide roller (guide device) 102 for guiding the sheet 2a to the bonding unit 200; second guide rollers (guide devices) 104a, 104b for guiding the sheet 2b to the bonding unit 200; an elastic element guide unit (guide device) 110 for supplying the elastic elements 10 to the bonding device 200; and a third guide roller 106 for guiding the bonded sheets and others, i.e., the composite stretchable member 1.

The bonding device 200 comprises an anvil roller (conveyance roller) 210, and a horn (clamping and pressing device) 220.

The anvil roller 210 is a rotary member rotatable about an axis extending in a direction perpendicular to a drawing sheet surface of FIG. 6. This direction orthogonal to the drawing sheet surface of FIG. 6 will hereinafter be referred to as "forward-rearward direction". The anvil roller 210 is operable, when rotated, to convey, on an outer peripheral surface thereof, the sheets 2a, 2b guided by the rollers 102, 104a, 104b and the elastic elements 10 guided by the elastic element guide unit 110 and sandwiched between the sheets 2a, 2b. In the example depicted in FIG. 6, the anvil roller 210 is configured to be rotated in a clockwise direction in FIG. 6. The sheets 2a, 2b sandwiching the elastic elements 10 will hereinafter be referred to occasionally as "pre-bonding sheets". The outer peripheral surface of the anvil roller 210 is formed with a plurality of convex sections 212 (see FIG. 11) each protruding radially outwardly. The derailed structure of the convex sections 212 will be described later.

The horn 220 is a device for giving ultrasonic vibration to the pre-bonding sheets being conveyed by the anvil roller 210, while clamping and pressing the pre-bonding sheets in cooperation with the outer peripheral surface of the anvil roller 210. The horn 220 is disposed to be opposed to the outer peripheral surface of the anvil roller 210. In the example depicted in FIG. 6, it is disposed to be opposed to a left side of the outer peripheral surface of the anvil roller 210. The horn 220 has an output portion 221 provided at a distal end thereof and configured to give ultrasonic vibration toward the outer peripheral surface of the anvil roller 210.

The horn 220 is operable to give ultrasonic vibration to the pre-bonding sheets, while pressing the output portion 221 against the pre-bonding sheets to clamp and press the pre-bonding sheets between the output portion 221 and the anvil roller 210. As a result, the sheets 2a, 2b are melted, and welded together. Further, each of the elastic elements 10 is also melted, so that the melted elastic elements 10 and the melted sheets 2a, 2b are welded together. Specifically, the output portion 221 is capable of clamping and pressing the pre-bonding sheets in cooperation with the aforementioned convex sections 212 to bond the sheets 2a, 2b together and further bond each of the elastic elements to the sheets 2a, 2b, in a region of the pre-bonding sheets disposed on the convex sections 212. The output portion 221 has a planar end face (see FIGS. 13 and 14).

In this embodiment, the covering layers 10b are formed using magnesium stearate having a lower melting point than that of the rubber strings 10a, as mentioned above. Thus, during welding of each of the elastic elements 10 to the sheets 2a, 2b, the covering layers 10b are melted without causing melting of the rubber strings 10a, and welded to the sheets 2a, 2b.

The distal end 221 of the horn 220 extends in the forward-rearward direction so as to enable the horn 220 to give ultrasonic vibration to the outer peripheral surface of the anvil roller 210 in the entire range in a direction of the rotational axis of the anvil roller 210. The horn 220 is operable to constantly give ultrasonic vibration during a period in which the pre-bonding sheets are conveyed by the anvil roller 210. Thus, along with conveyance of the pre-bonding sheets by the anvil roller 210, the pre-bonding sheets are continuously bonded together.

As depicted in FIG. 6, in this embodiment, the sheet 2a is introduced, via the first guide roller 102, onto the outer peripheral surface of the anvil roller 210 at a position P1 on a side opposite to the horn 220. Then, along with rotation of the anvil roller 210, the sheet 2a is conveyed toward the horn 220 along the outer peripheral surface of the anvil roller 210.

On the other hand, by means of the second guide rollers 104a, 104b, the sheet 2b is introduced onto the outer peripheral surface of the anvil roller 210 at a position P2 adjacent to the horn 220 and upstream of the horn 220 in a conveyance direction of the anvil roller 210, and conveyed to a position opposed to the horn 220.

The elastic elements 10 are introduced, via the elastic element guide unit 110, onto the outer peripheral surface of the anvil roller 210 at a position P3 between the position P1 at which the sheet 2a is introduced onto the anvil roller 210 and the position P2 at which the sheet 2b is introduced onto the anvil roller 210. In this way, the elastic elements 10 are conveyed to the position opposed to the horn 220 while being arranged between the sheets 2a, 2b.

The position P2 may be any position between the position P3 and the position opposed to the horn 220. However, it is set preferably to a position on the side of the position opposed to the horn 220, more preferably to a position adjacent to the position opposed to the horn 220. In this case, it becomes possible to prevent occurrence of displacement of the elastic elements 10 introduced onto the outer peripheral surface of the anvil roller 210 caused by the elastic elements 10 being promptly covered by the sheet 2b.

The elastic elements 10 are introduced onto the outer peripheral surface of the anvil roller 210 while lying side-by-side in the forward-rearward direction and in parallel relation to each other, and placed on the sheet 2a being previously conveyed on the outer peripheral surface of the anvil roller 210, while lying side-by-side in the width direction of the sheet 2a and in parallel relation to each other. Further, the elastic elements 10 are introduced onto the anvil roller 210 while being stretched in a circumferential direction of the anvil roller 210. In this embodiment, each of the elastic elements 10 is introduced onto the anvil roller 210 while being stretched by 300% with respect to a natural length thereof (on the assumption that the natural length is 100%).

The elastic element guide unit 110 comprises a plurality of elastic element guide rollers 111a, 111b, 111c, and a guide member 112.

The elastic element guide rollers 111a, 111b, 111c are rotary members each rotatable about an axis extending in the forward-rearward direction, and are configured to guide the elastic elements 10 toward the anvil roller 210 in a state in which each of the elastic elements 10 is stretched by 300% with respect to the natural length.

The guide member 112 is configured to introduce the elastic elements 10 onto the outer peripheral surface of the anvil roller 210, in a state where the plurality of elastic elements 10 are spaced apart from each other in the forward-rearward direction.

Figure 7:
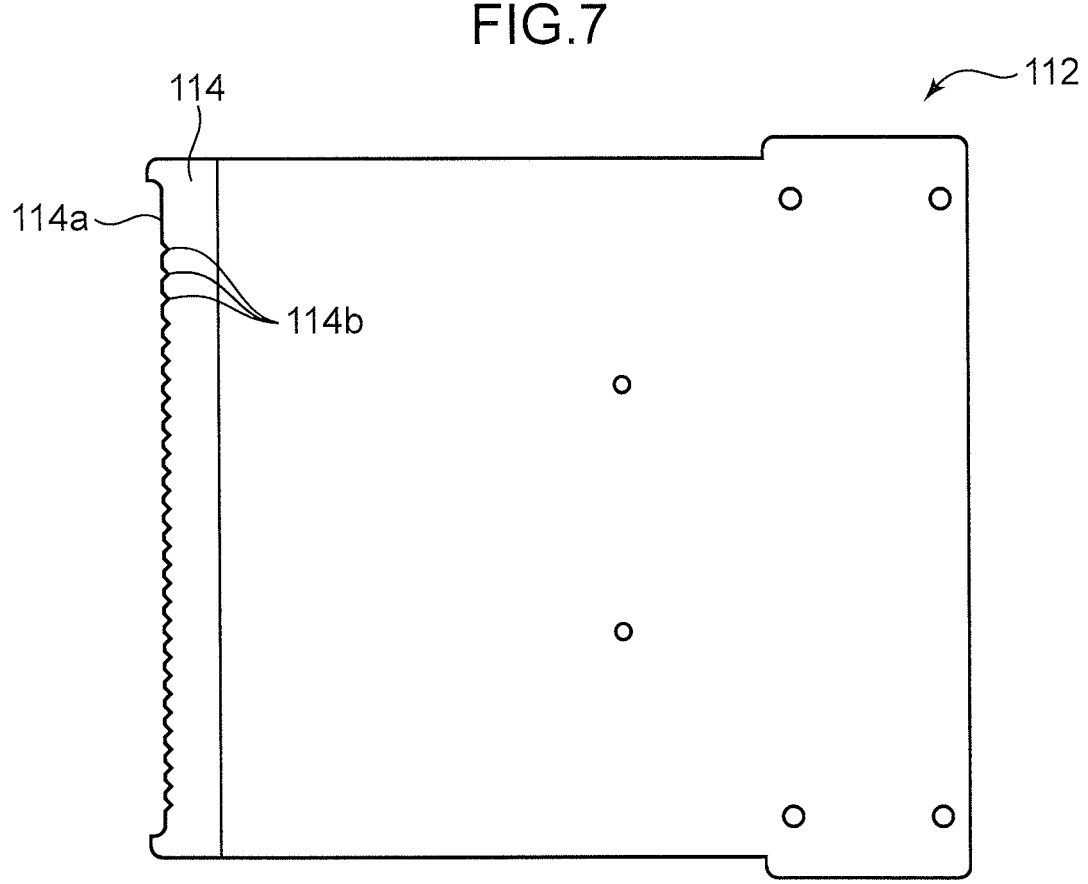
FIG. 7 is a plan view of a guide member.
Figure 8:
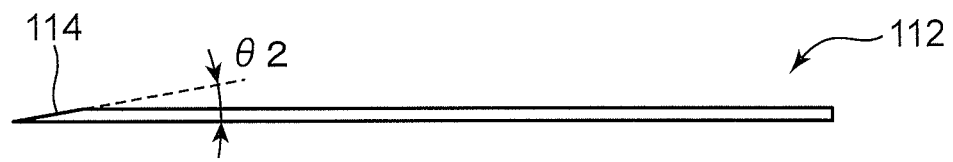
FIG. 8 is a side view of the guide member.

FIG. 7 is a plan view of the guide member 112. FIG. 8 is a side view of the guide member 112.

As depicted in FIGS. 7 and 8 and FIG. 6, the guide member 112 is a flat plate-shaped member. The guide member 112 has a distal edge opposed to the position P3 on the outer peripheral surface of the anvil roller 210, and a base edge disposed farther away from the anvil roller than the distal edge, wherein it is disposed to extend in a direction approaching and separating from the anvil roller 210 and extend in the forward-rearward direction. In this embodiment, in order to prevent interference between the guide member 112 and each of the sheets 2a, 2b, a thickness (in FIG. 8, a dimension in an upward-downward direction) of the guide member 112 is set to a small value, so that the guide member 112 has a thin-plate shape.

A distal edge region (region on the side of the anvil roller 210) of the guide member 112 is formed as an inclined portion 114 inclined to gradually come close to a bottom surface of the guide member 112 in a direction toward the distal edge, i.e., the guide member 112 is formed in a shape tapered toward the distal edge.

Figure 9:
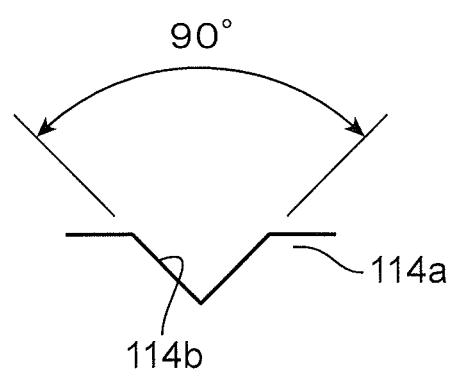
FIG. 9 is an enlarged diagram of a notch of the guide member.

A distal edge 114a of the inclined portion 114, i.e., the distal edge of the guide member 112, has a plurality of notches 114b formed side-by-side in the forward-rearward direction. These notches 114b lie side-by-side at equal intervals in the forward-rearward direction. As depicted in FIG. 9 which enlargedly depicts part of the notches 114b in FIG. 7, each of the notches 114b has a V shape which is concaved from the distal edge 114a of the inclined portion 114 toward the base edge to have an opening angle of 90 degrees. These notches 114b are configured to reliably position and hold the elastic elements 10 so as to guide the elastic elements 10 onto the outer peripheral surface of the anvil roller 210, in a state where the plurality of elastic elements 10 are spaced apart from each other in the forward-rearward direction. Further, the notches 114b are provided in opposed relation to and at the same intervals as those of aftermentioned grooves 214 formed in the anvil roller 210, so as to introduce the elastic elements 10, respectively, into the aftermentioned grooves 214.

Figure 10:
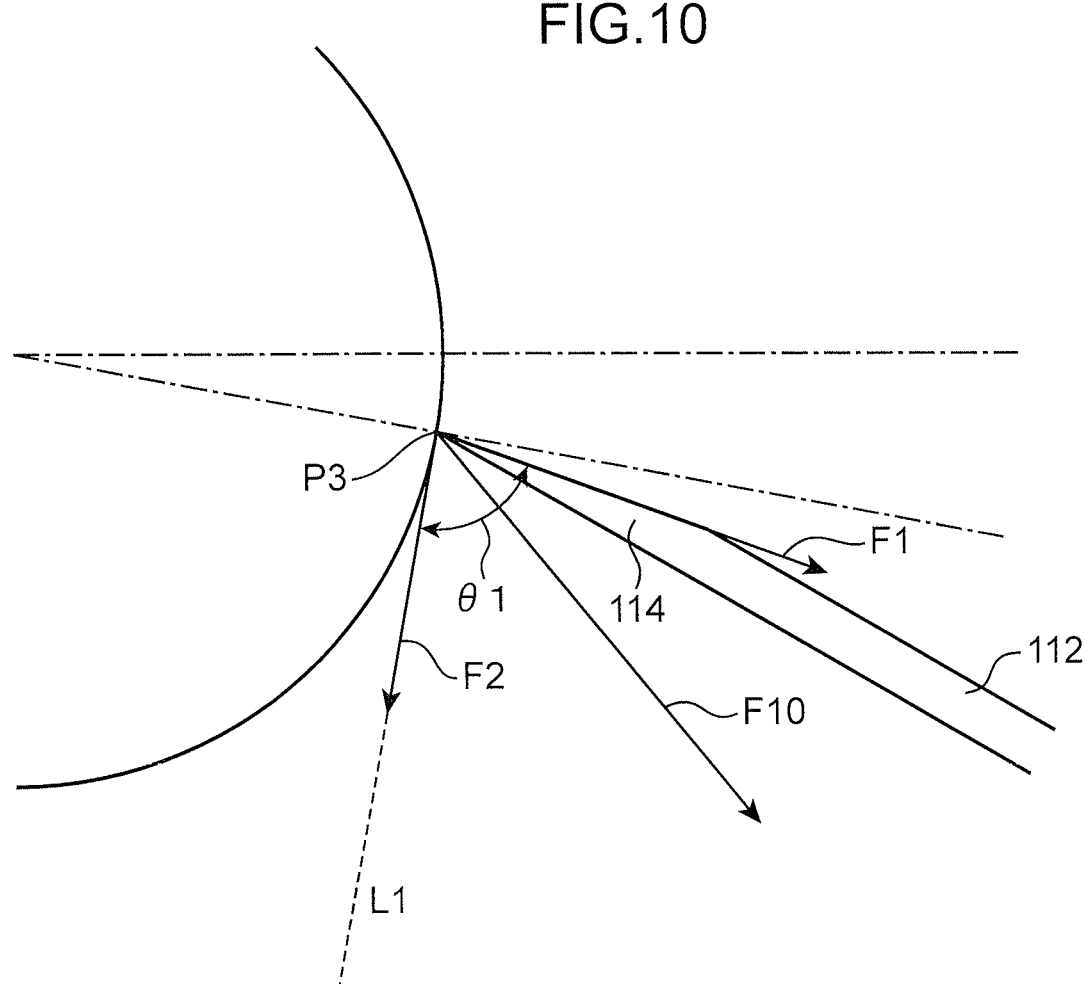
FIG. 10 is an enlarged diagram of part of FIG. 6.

As depicted in FIGS. 6 and 10, the guide member 112 is disposed such that an angle θ1 between a surface of the inclined portion 114 and a line tangent to the anvil roller 210 at the position P3 is 90 degrees or less, in side view. This is intended to suppress disengagement of the elastic elements from the notches 114b.

Specifically, when the angle between the surface of the inclined portion 114 and the line tangent to the anvil roller 210 at the position P3 is set to 90 degrees or less, a resultant force F10 of a force F1 caused by contraction force and applied to each of the elastic elements 10 on the inclined portion 114 (a pulling force acting in a direction separating from the anvil roller 210) and a force F2 applied from the anvil roller 210 to the elastic element 10 at the position P3 (a force F2 along the line tangent to the anvil roller at the position P3) can be set such that it is oriented in a direction approximately opposite to a conveyance direction of the elastic elements 10 on the inclined portion 114 (oriented in a direction toward the base edge of the guide member 112), as depicted in FIG. 10. That is, the resultant force F10 is applied to each of the elastic elements 10, in a direction causing the elastic element 10 to be pressed into a corresponding one of the notches 114b, so that it becomes possible to suppress disengagement of the elastic elements 10 from the notches 114b in the inclined portion 114.

In this embodiment, an angle θ1 between the surface of the inclined portion 114 and a line L1 which is part of the tangent line to the anvil roller 210 passing through the position P3, and located downstream of the position P3 in the conveyance direction of the anvil roller 210, is set to become approximately 90 degrees, and the guide member 112 is set at a position free from interference with the sheets 2a, 2b, as mentioned above. Specifically, in this embodiment, the position P3 is set at a position rotated downstream in the conveyance direction by about 10 degrees with respect to a line passing through a center of the anvil roller 210 and extending horizontally, and an angle θ2 (see FIG. 8) of the inclined portion 114 with respect to the bottom surface of the guide member 112 is set to 10 degrees.

Figure 11:
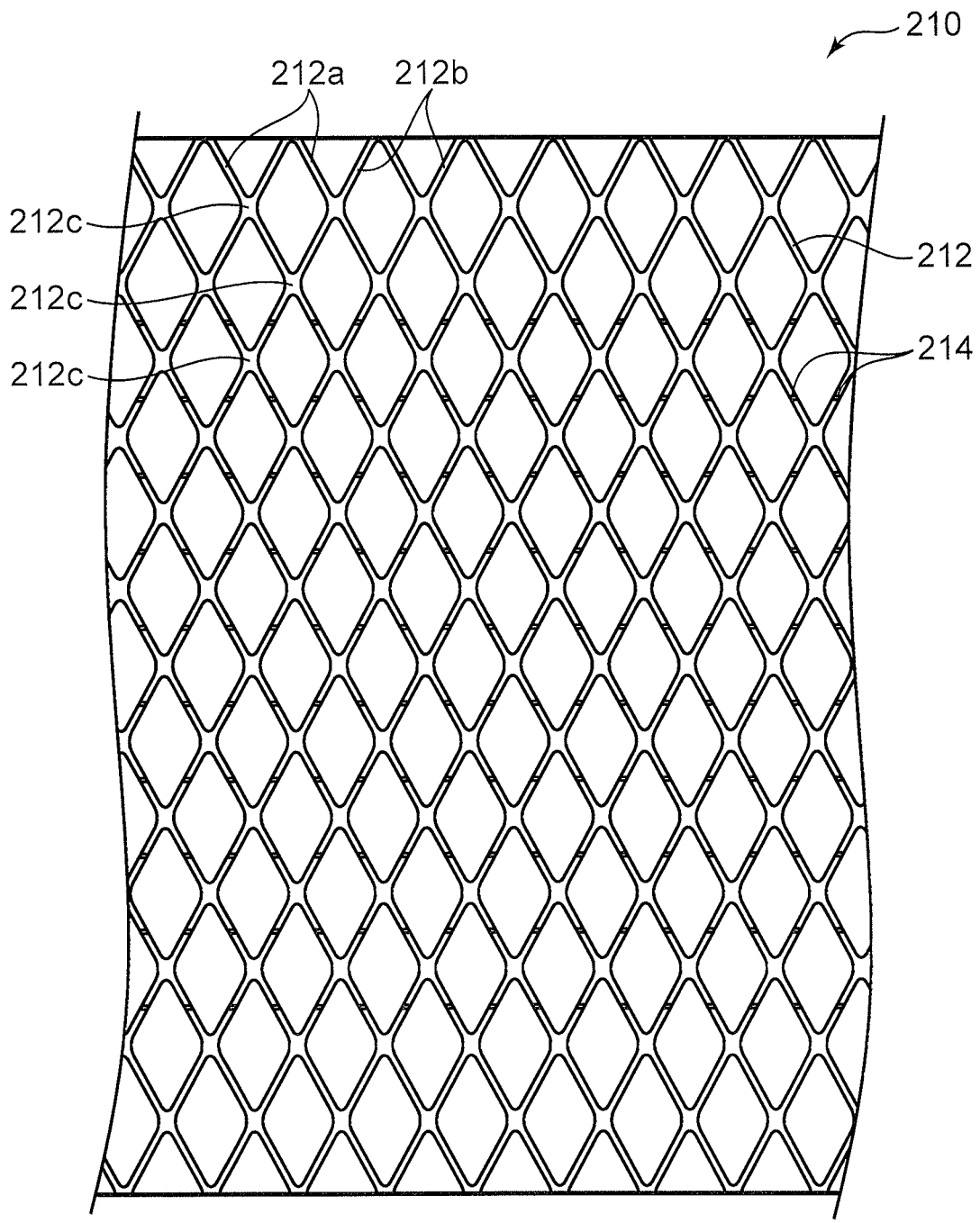
FIG. 11 is a diagram depicting an outer peripheral surface of an anvil roller.

The outer peripheral surface of the anvil roller 210 is formed with the convex sections 212 each protruding radially outwardly, as depicted in FIG. 11. The convex sections 212 are provided on the outer peripheral surface of the anvil roller 210 over the entire circumferential direction thereof. The convex sections 212 have a shape corresponding to that of the bonding sections 4. In this embodiment, the bonding sections 4 have a diamond-lattice pattern as mentioned above, and correspondingly the convex sections 212 have a diamond-lattice pattern.

Specifically, the convex sections 212 comprise a first convex section 212a for forming the first bonding section 4a, and a second convex section 212b for forming the second bonding section 4b.

The first convex section 212a extends along a direction (first direction) intersecting the circumferential direction of the anvil roller 210 (conveyance direction of the anvil roller 210), i.e., along a line intersecting the circumferential direction, and a plurality of the first convex sections 212a are arranged in parallel relation to each other and at equal intervals in the circumferential direction. The second convex section 212b extends along a direction (second direction) intersecting the circumferential direction of the anvil roller 210 and the first direction, i.e., along a line intersecting the circumferential direction, and a plurality of the second convex sections 212b are arranged in parallel relation to each other and at equal intervals in the circumferential direction of the anvil roller 210.

Each of the first convex sections 212a and the second convex sections 212b is inclined at an angle of less than 45 degrees with respect to the forward-rearward direction, and the intersecting convex sections are inclined in symmetrical relation to each other with respect to the forward-rearward direction. Further, a spaced-apart distance between adjacent ones of the first convex sections 212a is coincident with a spaced-apart distance between adjacent ones of the second convex sections 212b, and intersection points 212c of the first convex sections 212a with the second convex sections 212b lie side-by-side at equal intervals on each of two line extending, respectively, in the forward-rearward direction and the circumferential direction of the anvil roller 210.

Figure 12:
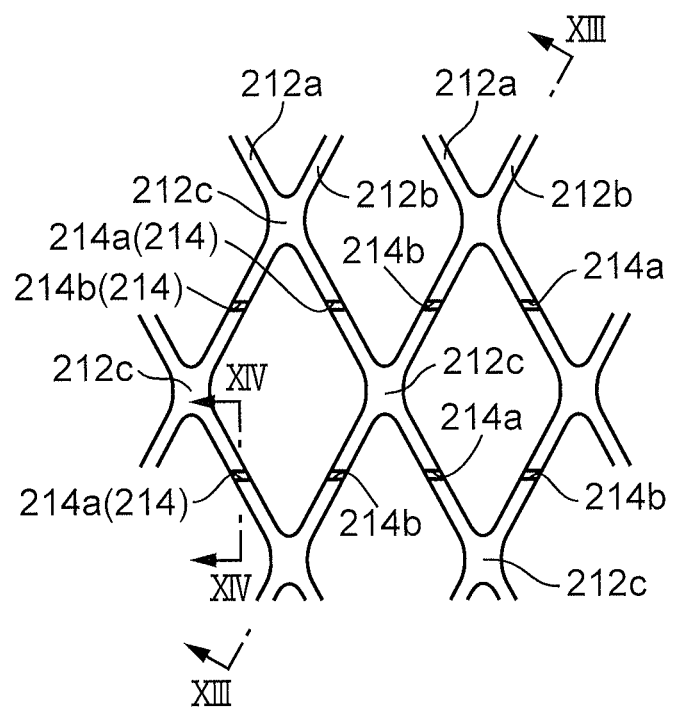
FIG. 12 is a diagram enlargedly depicting part of FIG. 11.
Figure 13:
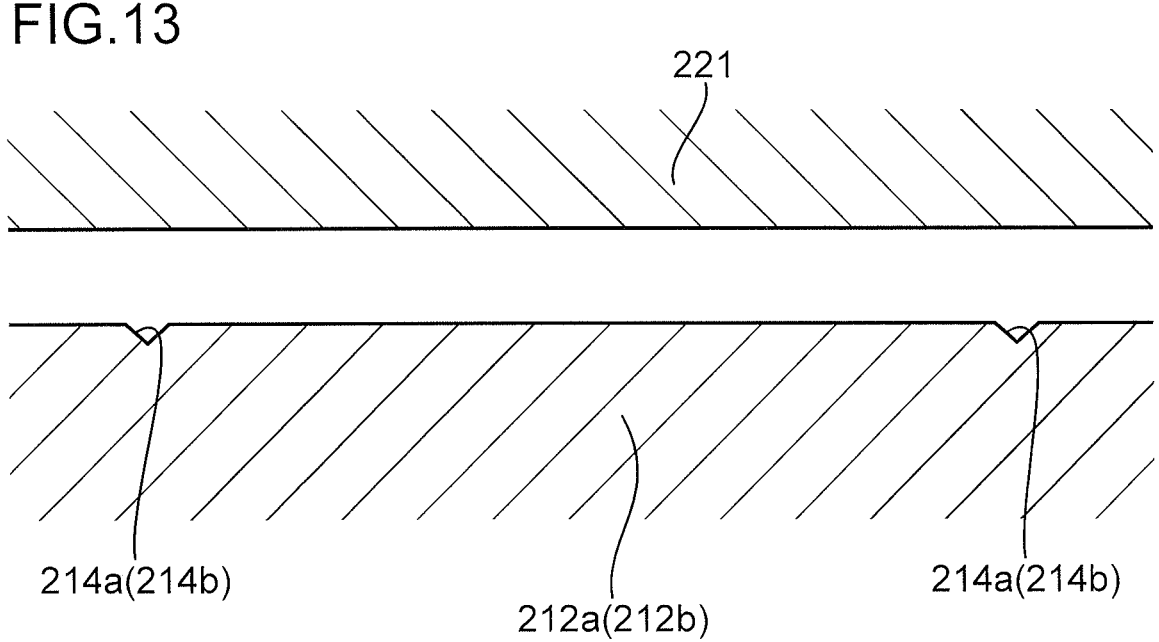
FIG. 13 is a sectional view taken along the line XIII-XIII in FIG. 12.
Figure 14:
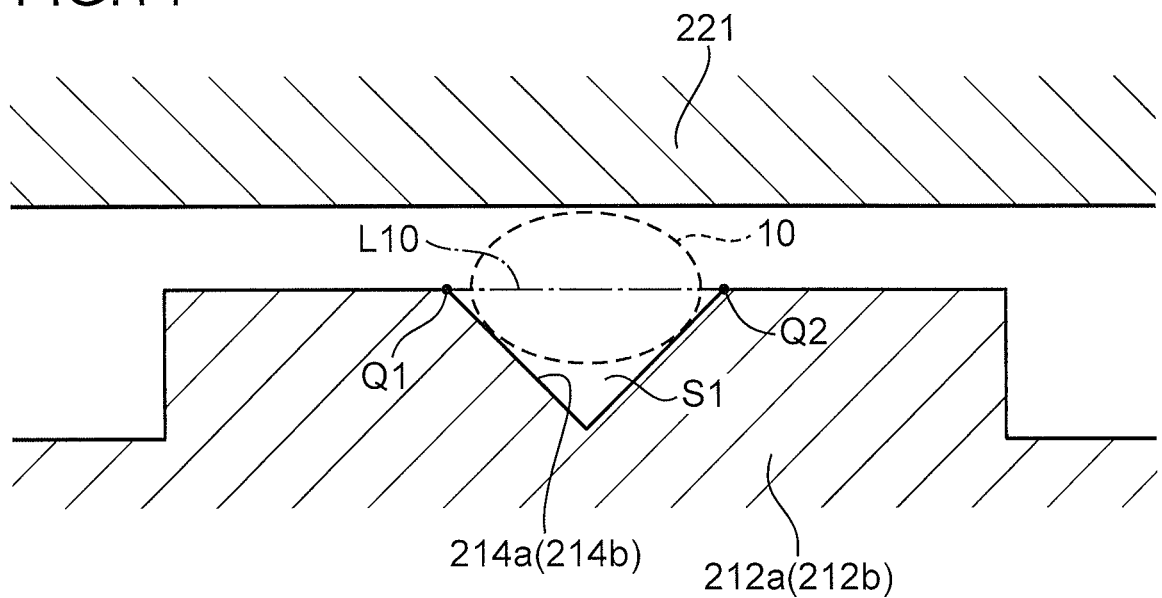
FIG. 14 is a sectional view taken along the line XIV-XIV in FIG. 12.

As depicted in FIG. 12 which is an enlarged view of part of FIG. 11, FIG. 13 which is a sectional view taken along the line XIII-XIII in FIG. 12, and FIG. 14 which is a sectional view taken along the line XIV-XIV in FIG. 12, each of the first convex sections 212a and the second convex sections 212b is formed with a plurality of grooves 214 (214a, 214b) each concaved inwardly in a radial direction of the anvil roller 210. As depicted, for example, in FIG. 13, each of the first convex sections 212a and the second convex sections 212b is formed with a plurality of grooves 214 at positions spaced apart from each other in a longitudinal direction thereof.

A plurality of regions of the sheet 2a (sheet disposed on the side of the anvil roller 210) on each of which a respective one of the elastic elements 10 will lie are inserted, respectively, in a plurality of groups of the grooves 214. Therefore, the arrangement of the elastic elements 10 with respect to the bonding sections 4 is identical to the arrangement of the groups of grooves with respect to the convex sections 212.

Specifically, in this embodiment, as depicted in FIG. 12, a groove (first groove) 214a extending in the circumferential direction of the anvil roller 210 is formed in each of the first convex sections 212a, at a position between adjacent ones of the intersection points 212c with the second convex sections 212b, more specifically, at a central position between the adjacent intersection points 212c. Similarly, a groove (second groove) 214b is formed in each of the second convex sections 212b, at a position between adjacent ones of the intersection points 212c with the first convex sections 212a, more specifically, at a central position between the adjacent intersection points 212c. Further, a plurality of the grooves 214 are provided on a line extending along the circumferential direction of the anvil roller 210 at equal intervals, and provided on a line extending along the forward-rearward direction at equal intervals.

The sheet 2a is conveyed by the anvil roller 210, in a state in which the regions of the sheet 2a on each of which a respective one of the elastic elements 10 lies are inserted, respectively, in grooves 214. As mentioned above, in this embodiment, each of the elastic elements 10 is introduced into a respective one of the grooves 214 by the guide member 112 having the notches 114 provided at respective positions corresponding to the grooves 214, so that the elastic elements 10 are stably disposed, respectively, at appropriate positions on the sheet 2a.

In this embodiment, the sheet 2a is conveyed by the anvil roller 210, in a state in which each of the elastic elements 10 is partially inserted in a respective one of the grooves 214, together with part of the sheet 2a. It should be noted that the sheet 2a may be conveyed in a state in which only the part of the sheet 2a is inserted.

As above, the grooves 214 are formed, respectively, in the regions of the convex sections 212 on each of which a respective one of the elastic elements 10 will lie. Thus, when the pre-bonding sheets are clamped and pressed during bonding, at least part of each of the elastic elements 10 arranged between the pre-bonding sheets is moved into a corresponding one of the grooves in an escaping manner. This makes it possible to avoid breakage of the elastic elements 10 during clamping and pressing.

However, if each of the grooves 214 has an excessively large cross-sectional area, it could become difficult to appropriately bond each of the elastic elements 10 to the sheets 2*a*, 2*b*. For this reason, in this embodiment, as depicted in FIG. 14, each of the elastic elements 10 having a natural length is disposed in a corresponding one of the grooves 214, in such a manner that part of the elastic element 10 protrudes outside the grooves 214, and the remaining part of the elastic element 10 is received in the grooves 214. More specifically, a cross-sectional shape of the groove 214 cut along a plane orthogonal to the circumferential direction (conveyance direction) of the anvil roller 210 is set such that, in the state in which the elastic element 10 having a natural length is disposed in the groove 214, part of the elastic element 10 protrudes outwardly in the radial direction of the anvil roller 210, with respect to a linear imaginary line (one-dot chain line) L10 connecting opening edges (Q1, Q2) of the groove 214. Further, the above cross-sectional shape of the groove 214 is set such that, when the elastic element 10 being stretched by 300% is disposed in the groove 214, part of the elastic element 10 protrudes outwardly in the radial direction of the anvil roller 210, with respect to the linear imaginary line L10 connecting the opening edges (Q1, Q2) of the groove 214. Such a cross-sectional shape of the groove 214 is preferably an approximately V shape, as depicted in FIG. 14. Further, a cross-sectional area S 1 of the groove 214 is preferably set to be less than a cross-sectional area of the elastic element 10 to be disposed therein.

(3) Production Method

A method of producing the composite stretchable member 1 using the production apparatus 100 configured as described above comprises a guide step and a bonding step.

The guide step includes: guiding the sheet 2*a* to the bonding device 200 by the first guide roller 102; guiding the sheet 2*b* to the bonding device 200 by the second guide rollers 104*a*, 104*b*; and guiding the elastic elements 10 to the bonding device 200 by the elastic element guide unit 110. Further, in the guide step, the sheets 2*a*, 2*b* and the elastic elements 10 are conveyed to the bonding device 200, in a state in which the elastic elements 10 are sandwiched between the sheets 2*a*, 2*b* while being arranged to extend in the longitudinal direction of the sheets 2*a*, 2*b* in parallel relation to each other.

In this embodiment, the sheets 2*a*, 2*b* and the elastic elements 10 are guided to the outer peripheral surface of the anvil roller 210, as mentioned above.

Further, by the guide member 112, the regions of the sheet 2*a* on each of which a respective one of the elastic elements 10 lies, and parts of the elastic elements 10, are introduced, respectively, into the grooves 214 formed in the convex sections 212.

The bonding step includes: clampingly pressing the pre-bonding sheets, i.e., the sheets 2*a*, 2*b* between which the elastic elements 10 are sandwiched, by the horn 220 and the convex sections 212; and, in this state, giving ultrasonic vibration from the horn 220 toward the convex sections 212 to bond each of the elastic elements 10 to the sheets 2*a*, 2*b* and further bond the sheets 2*a*, 2*b* together, by means of ultrasonic welding. In this process, associated ones of the regions of the anvil roller-side sheet 2*a* on each of which a respective one of the elastic elements 10 lies, and parts of the elastic elements 10, are partially welded together, in the state in which they are inserted in a corresponding one of the grooves 214.

(4) Wearable Article and Production Method Therefor

Figure 15:
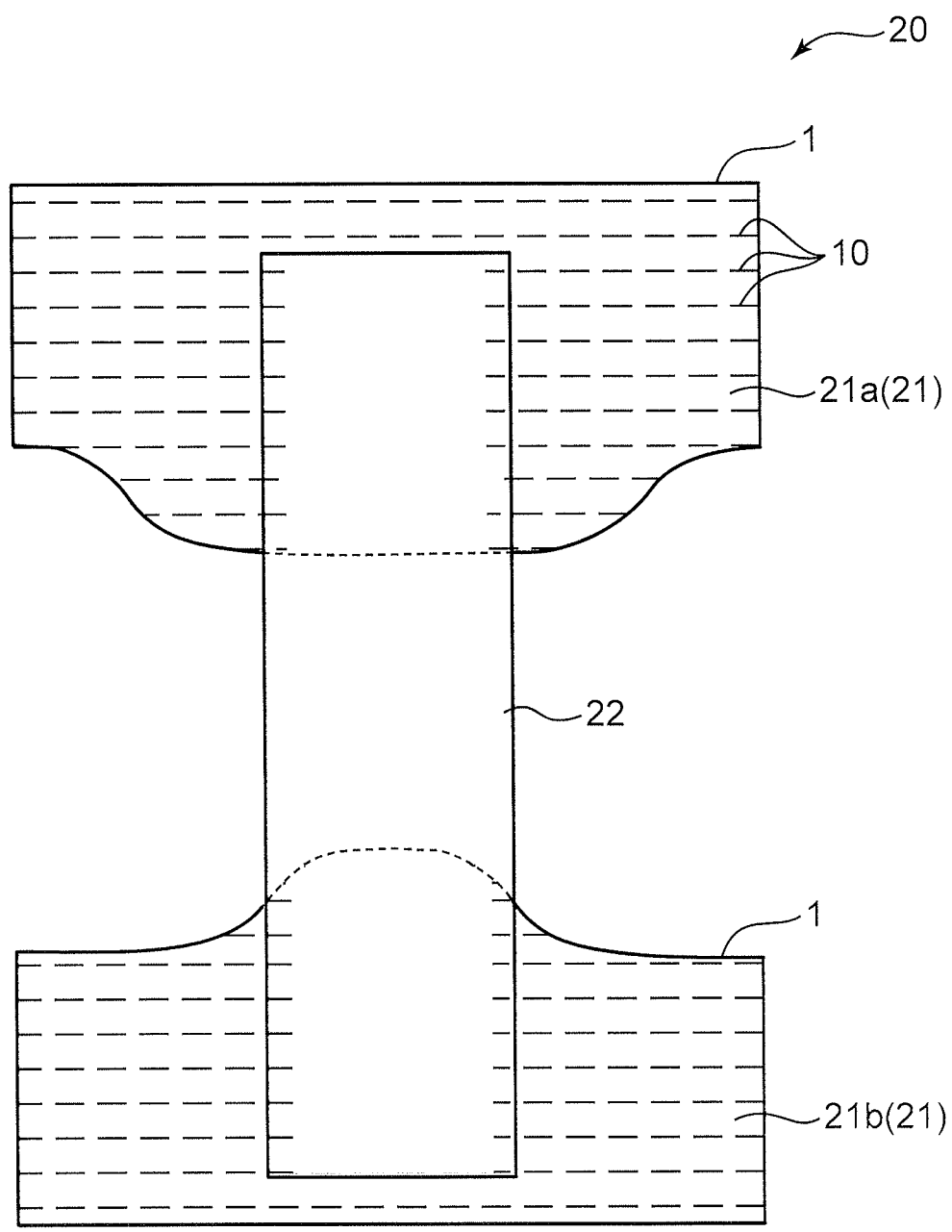
FIG. 15 is a developed diagram of a disposable diaper using the composite stretchable member.

FIG. 15 is a schematic diagram depicting a disposable diaper (wearable article) 20 using the composite stretchable member 1 configured as described above, as a usage example of the composite stretchable member 1.

The disposable diaper 20 comprises: a waist portion 21 having a front abdominal portion 21*a* to be disposed on a front side of an abdominal region of a wearer, and a rear dorsal portion 21*b* to be disposed on the side of a hip region of the wearer; and a crotch portion 22 to be disposed along a crotch region of the wearer. The composite stretchable member 1 according to this embodiment is used in the front abdominal portion 21*a* and the rear dorsal portion 21*b*. For example, the composite stretchable member 1 is applied to the front abdominal portion 21*a* and the rear dorsal portion 21*b* in such a manner that a stretchable direction of the composite stretchable member 1 is coincident with a waist circumferential direction during wearing (a rightward-leftward direction in FIG. 15).

FIG. 16 is a diagram illustrating a production method for the disposable diaper 20. This production method comprises stages 1 to 3. In the stage 1, one pair of continuous bodies 101 of the composite stretchable member 1 extending in a conveyance direction are prepared. That is, a continuous body 101 for forming the front abdominal portion 21*a* and a continuous body 101 for forming the rear dorsal portion 21*b* are prepared. Then, the pair of continuous bodies 101 are conveyed in a longitudinal direction of each of the continuous bodies 101 while being arranged parallel to each other, and the crotch portion 22 is placed to straddle the pair of continuous bodies 101, in such a manner that a longitudinal direction of the crotch portion 22 is oriented orthogonal to the longitudinal direction of the continuous body 101. For example, a plurality of the crotch portions 22 are placed in spaced-apart relation in the conveyance direction. Then, the crotch portions 22 and the continuous bodies 101 are bonded together to form a bonded body 102 (bonded body forming step).

Subsequently, in the stage 2, a hole serving as a leg opening is formed between adjacent ones of the crotch portions 22. Then, the bonded body 102 is double-folded along a folding line defined by a center line of the bonded body 102 in a width direction (a direction orthogonal to the longitudinal direction of the continuous body 101), in such a manner that each of the crotch portions 22 is located inward of the continuous bodies 101 (double-folding step).

Subsequently, in the stage 3, superimposed portions of the continuous bodies 101 at an intermediate position between adjacent ones of the crotch portions 22 are bonded together along a direction orthogonal to the longitudinal direction of the continuous body 101, to thereby form a side seal (side sealing step), and the continuous bodies 101 are cut along a cutting line K in the side seal (cutting step).

In this way, the disposable diaper 20 is produced in which the waist portion 21 (the front abdominal portion 21*a* and the rear dorsal portion 21*b*) is formed of the composite stretchable members 1 so as to be stretchable in the waist circumferential direction.

In this embodiment, the sub-step of providing a hole serving as a leg opening may be performed before bonding the crotch portions 22 to the continuous bodies 101, or needs not necessarily be performed. Further, each of the elastic elements 10 of the composite stretchable member 1 may be bonded to the two sheets 2*a*, 2*b* by a hot-melt adhesive, in a vicinity of a region corresponding to the cutting line K. This makes it possible to prevent drop-off of the elastic elements 10 due to cutting along the cutting line K.

As described above, the production apparatus for the composite stretchable member 1 according to this embodiment comprises: the bonding device 200 operable to ultrasonic-weld and bond each of the elastic elements 10 to the sheets 2a, 2b and further bond the sheets 2a, 2b together, in the state in which the elastic elements 10 are sandwiched between the two sheets 2a, 2b; and the first guide roller 102, the second guide roller 104 and the elastic element guide unit 110 each operable to guide a respective one of the sheet 2a, the sheet 2b and a group of the elastic elements 10, to the bonding device 200. The bonding device 200 is provided with: the anvil roller 210 having an outer peripheral surface formed with the convex section 212 protruding radially outwardly and designed to convey the sheets 2a, 2b with the elastic elements 10 sandwiched therebetween, along the longitudinal direction of the sheets 2a, 2b; and the horn 220 comprising the output portion 221 for giving ultrasonic vibration to the anvil roller 210, wherein the output portion 221 and the convex section 212 are configured to ultrasonic-weld each of the elastic elements 10 to the sheets 2a, 2b and further ultrasonic-weld the sheets 2a, 2b together, in a cooperative manner.

Therefore, as compared to the case where the bonding is performed using a hot-melt material, it becomes unnecessary to prepare the hot-melt material. Further, it is possible to bond together the two sheets with the elastic elements 10 therebetween, while conveying the two sheets by the anvil roller 210, so that, as compared to the case where a device for applying a hot-melt material is provided, it becomes possible to simplify production equipment to suppress power consumption. That is, it is possible to bond the sheets 2a, 2b together and further bond each of the elastic elements 10 to the sheets 2a, 2b, with a simplified configuration.

In this production apparatus, ultrasonic welding is performed under a condition that components to be welded together are pressed, so that there is a possibility that the elastic elements 10 are damaged during the pressing. Considering this, in the production apparatus 100, the groove 214 are formed on the convex section 212 for pressing the sheets 2a, 2b with the elastic elements 10 sandwiched therebetween, in cooperation with the output portion 211. Thus, during the pressing, the elastic elements 10 are allowed to escape into the grooves 214. This makes it possible to keep down a pressure to be applied to the elastic elements 10, to thereby suppress damage to the elastic elements 10.

Further, in the production apparatus 100, the convex section 212 extends in a direction intersecting the conveyance direction of the anvil roller 210, and the grooves 214 are provided on the convex section 212 at positions spaced apart from each other in the longitudinal direction of the convex section 212. Thus, it is possible to continuously bond the sheets 2a, 2b together along a direction intersection the conveyance direction, while allowing the elastic elements 10 to escape into the grooves 214. This makes it possible to more strongly bond the sheets 2a, 2b together while suppressing damage to the elastic elements 10.

Further, the above embodiment can bring out the following advantageous effects.

In the above embodiment, a cross-sectional shape of each of the grooves 214 taken along a plane orthogonal to the conveyance direction of the anvil roller 210 is set such that, when each of the elastic elements 10 is disposed in a corresponding one of the grooves 214 in a state in which the elastic element has a natural length, a part of the elastic element 10 disposed in the groove 214 protrudes outwardly in the radial direction of the anvil roller 210 with respect to the linear imaginary line L10 connecting the opening edges (Q, Q2) of the groove 214.

Thus, during the ultrasonic welding, it is possible to moderately press each of the elastic elements 10 disposed in a corresponding one of the grooves 214, and the sheets 2a, 2b, to bond them together, while allowing the elastic element 10 to escape into this groove. This makes it possible to more reliably bond each of the elastic elements 10 to the sheets 2a, 2b while suppressing damage to the elastic elements 10. More specifically, it is possible to allow a portion of each of the elastic elements 10 located inwardly with respect to the imaginary line L10 connecting the opening edges Q1, Q2 of a corresponding one of the grooves 214, i.e., received inside the groove 214, to escape toward an inner side of the groove 214 (a side farther away from the horn 220), by appropriately applying a pressure to the remaining portion of the elastic element 10 protruding outwardly with respect to the imaginary line L10 connecting the opening edges Q1, Q2 of the groove 214, and the sheets 2a, 2b. This makes it possible to suppress damage to the elastic elements 10 while ensuring a bonding force between associated ones of the elastic elements 10 and the sheets 2a, 2b.

In particular, the aforementioned cross-sectional shape of the groove 214 is set such that, when the elastic element 10 being stretched by 300% is disposed in the grooves, a part of the elastic element 10 protrudes outwardly in the radial direction of the anvil roller 214 with respect to the linear imaginary line L10 connecting the opening edges (Q1, Q2) of the groove 214.

This makes it possible to more appropriately apply a pressure to the sheets 2a, 2b and the elastic elements 10 to more reliably bond them together, while suppressing damage to the elastic elements 10.

In this embodiment, each of the elastic elements 10 is composed of an elastic element comprising the plurality of elastic bodies 10a, and the covering layers 10b each covering a respective one of at least part of the elastic bodies 10a, wherein the covering layers 10b are melted and welded to the sheets 2a, 2b, whereby each of the elastic elements 10 is bonded to the sheets 2a, 2b.

This makes it possible to suppress damage to the elastic bodies 10a due to welding.

In this embodiment, the elastic element guide unit 110 for guiding the elastic elements 10 to the anvil roller 210 comprises the guide member 112 configured to extend in a direction away from a position adjacent to the outer peripheral surface of the anvil roller 210, and to guide the elastic elements 10 to the outer peripheral surface of the anvil roller 210, in a state where the plurality of elastic elements 10 are spaced apart from each other in a direction parallel to the axis of the anvil roller 210. Further, the distal edge of the guide member 112 is formed with the plurality of notches 114b each for holding a respective one of the elastic elements 10, at positions spaced apart from each other in a direction parallel to the axis of the anvil roller.

This makes it possible to more reliably guide, to the anvil roller 210, the elastic elements 10 at appropriate positions, i.e., at positions spaced apart from each other in a direction parallel to the axis of the anvil roller. Particularly, in this embodiment, the notches 114b are arranged at positions corresponding to the grooves 214, so that it is possible to more reliably set the elastic elements 10, respectively, in the grooves 214 to allow the elastic elements 10 to escape into the grooves 214 during welding to thereby suppress damage to the elastic elements 10.

In this embodiment, the convex section comprises: the plurality of first convex sections 212a extending parallel to each other along a first direction intersecting the conveyance direction of the anvil roller 210; and the plurality of second convex sections 212b extending parallel to each other along a second direction intersecting the conveyance direction of the anvil roller 210 and the first direction, and each intersecting the first convex sections 212a.

As a result, the bonding sections 4 in the composite stretchable member 1 formed by the convex section 212 comprise: the plurality of first bonding sections 4a extending parallel to each other along a first direction intersecting the longitudinal direction of the sheets 2a, 2b (the stretchable direction of the composite stretchable member 1); and the plurality of second bonding sections 4b extending parallel to each other along a second direction intersecting the longitudinal direction of the sheets 2a, 2b and each intersecting the first bonding sections.

That is, the sheets 2a, 2b are bonded together in the two types of bonding sections 4a, 4b extending in different directions. Thus, even in a situation where an external force is applied to the composite stretchable member 1 from various directions, it is possible to more reliably suppress debonding between the sheets 2a, 2b or between associated ones of the sheets 2a, 2b and the elastic elements 10. Further, the first bonding sections 4a and the second bonding sections 4b intersect each other, so that it is possible to increase a bonding force between the sheets 2a, 2b in the vicinity of each of the intersection points 4c, and thus increase a bonding force of the composite stretchable member 1 at each of the intersection points 4c.

In this embodiment, each of the first direction and the second direction is set to a direction intersecting a direction orthogonal to the circumferential direction of the anvil roller 210 (the conveyance direction of the anvil roller 210).

As a result, in the composite stretchable member 1, the first direction of the first bonding sections 4a and the second direction of the second bonding sections 4b set to a direction intersecting a direction orthogonal to the longitudinal direction of the sheets 2a, 2b (the stretchable direction of the composite stretchable member 1).

Thus, when an external force is applied to the first bonding sections 4a and the second bonding sections 4b in the longitudinal direction of the sheets 2a, 2b, it is possible to reduce a normal component of the external force with respect to each of the bonding sections 4a, 4b and thus reduce a force to be applied in a direction perpendicular to each of the bonding sections 4a, 4b. This makes it possible to more reliably suppress debonding between the sheets 2a, 2b in the bonding sections 4a, 4b.

In this embodiment, each of the first direction and the second direction is inclined at an angle of less than 45 degrees, with respect to the direction orthogonal to the conveyance direction of the anvil roller.

As a result, in the composite stretchable member 1, each of the first bonding sections 4a and the second bonding sections 4b can be formed such that it is inclined at an angle of less than 45 degrees, with respect to the width direction of the sheets 2a, 2b (a direction orthogonal to the stretchable direction of the composite stretchable member 1).

Thus, it is possible to reduce a distance between the intersection points 4d, 4e of each of the elastic elements 10 with the bonding sections 4a, 4b, i.e., a distance between the bonded points 4d, 4e of each of the elastic elements 10 to the sheets 2a, 2b (a distance between adjacent ones of the bonded points 4d, 4e) in the longitudinal direction of the sheets 2a, 2b (the stretchable direction of the composite stretchable member 1). This makes it possible to more finely form gathers between the bonded points 4d, 4e in the stretchable direction, in a non-stretched state of the composite stretchable member 1. Therefore, it is possible to provide a better feel.

In this embodiment, the intersection points 212c of the first convex sections 212a with the second convex sections 212b lie in a line extending in the circumferential direction of the anvil roller 210 (the conveyance direction of the anvil roller 210), and lie in a straight line extending in the direction orthogonal to the conveyance direction of the anvil roller 210.

As a result, in the composite stretchable member 1, the intersection points 4c of the first bonding sections 4a with the second bonding sections 4b lie in a straight line extending in the longitudinal direction of the sheets 2a, 2b (the stretchable direction of the composite stretchable member 1), and lie in a straight line extending in the width direction of the sheets 2a, 2b (the direction orthogonal to the stretchable direction of the composite stretchable member 1).

Thus, the intersection points 4c of the first and second bonding sections 4a, 4b can be arranged in an orderly manner, so that it is possible to form gathers between adjacent ones of the intersection points 4c of the first and second bonding sections 4a, 4b in a regular pattern so as to increase a bonding force between the sheets 2a, 2b in the longitudinal and width directions of the sheets 2a, 2b.

In this embodiment, the grooves 214 are formed in regions of the first and second convex sections 212a, 212b other than the intersection points 212c of the first convex sections 212a with the second convex sections 212b.

As a result, in the composite stretchable member 1, each of the elastic elements 10 scan be disposed such that it intersects the first bonding sections 4a and the second boding sections 4b at points other than the intersection points 4c.

That is, each of the elastic elements 10 is bonded to the sheets in the first bonding sections 4a and the second boding sections 4b, individually. In this case, as compared to the case where each of the elastic elements 10 is disposed to intersect the bonding sections 4a, 4b at the intersection points 4c thereof, it is possible to increase the number of bonded points of each of the elastic elements 10 to the sheets 2a, 2b. This makes it possible to increase a bonding force between associated ones of the elastic elements 10 and the sheets 2a, 2b.

In this embodiment, the grooves 214a formed on the first convex sections 212a and the grooves 214b formed on the second convex sections 212b lie in a straight line extending in a direction orthogonal to the circumferential direction of the anvil roller 210 (the conveyance direction of the anvil roller 210).

As a result, in the composite stretchable member 1, the intersection points 4d of the elastic elements 10 with the first bonding sections 4a, and the intersection points 4e of the elastic elements 10 with the second bonding sections 4b, lie in a straight line extending in the width direction of the sheets 2a, 2b (the direction orthogonal to the stretchable direction of the composite stretchable member 1).

Thus, it is possible to form gathers between adjacent ones of the bonded points of each of the elastic elements 10 to the sheets 2a, 2b, i.e., between adjacent ones of the elastic element-side intersection points 4d, 4e, in such a manner as to lie in a straight line extending in the width direction of the sheets 2a, 2b, thereby providing good appearance. Further, it is possible to provide a better feel in this direction.

In this embodiment, the grooves 214 are provided at equal intervals in the circumferential direction of the anvil roller 210 (the conveyance direction of the anvil roller 210).

As a result, in the composite stretchable member 1, intersection points of each of the elastic elements 10 with the bonding sections 4, i.e., bonded points of each of the elastic elements 10 to the sheets 2a, 2b, are formed at equal intervals in the longitudinal direction of the sheets 2a, 2b so as to allow the elastic elements 10 and the bonding sections 4 to intersect each other at equal intervals in the longitudinal direction of the sheets 2a, 2b (the stretchable direction of the composite stretchable member 1). That is, each of the elastic elements 10 intersects the bonding sections 4 at equal intervals in the longitudinal direction of the sheets 2a, 2b.

Thus, sizes of gathers formed between adjacent ones of the bonded points 4d, 4e of each of the elastic elements 10 to the sheets 2a, 2b, specifically, dimensions of the gathers protruding outwardly, i.e., in a direction perpendicular to the sheets 2a, 2b, can be uniformed in the longitudinal direction of the sheets 2a, 2b (the stretchable direction of the composite stretchable member 1). This makes it possible to provide good appearance and good feel.

As above, in this embodiment, the production apparatus 100 comprising the anvil roller 210 and the guide device makes it possible to bond the sheets 2a, 2b together and further bond each of the elastic elements 10 to the sheets 2a, 2b, with a high bonding force, without damaging the elastic elements 10. Thus, by producing a composite stretchable member 1 using the production apparatus 100, it is possible to obtain the composite stretchable member 1 in which each of the elastic elements 10 is strongly bonded to the sheets 2a, 2a, while suppressing damage to the elastic elements 10.

It should be noted that the present invention is not limited to the above embodiment. For example, the following embodiments may be employed.

Although the above embodiment has been described based on an example where the cross-sectional shape of each of the grooves 214 is an approximately V shape, the cross-sectional shape is not limited thereto, but may be a semi-circular shape or the like.

Further, each of the grooves 214 may have a sectional area equal to or greater than that of each of the elastic elements 10 to be disposed therein.

The anvil roller 210 in the above embodiment, i.e., a conveyance roller having the convex section 212 protruding radially outwardly and having an outer peripheral surface for conveying the sheets 2a, 2b with the elastic elements 10 sandwiched therebetween, in the longitudinal direction of the sheets 2a, 2b, may be configured to give ultrasonic vibration to the sheets 2a, 2b. Further, in place of the horn 220 in the above embodiment, a member having a distal end formed with a flat surface extending in the forward-rearward direction may be used as a clamping and pressing device operable to clamp and press the two sheets 2a, 2b in cooperation with the outer peripheral surface of the conveyance roller, more specifically, the convex section 212. In this case, ultrasonic vibration may be given from the convex section 212 toward the flat surface.

The guide member 112 may be omitted.

Figure 17:
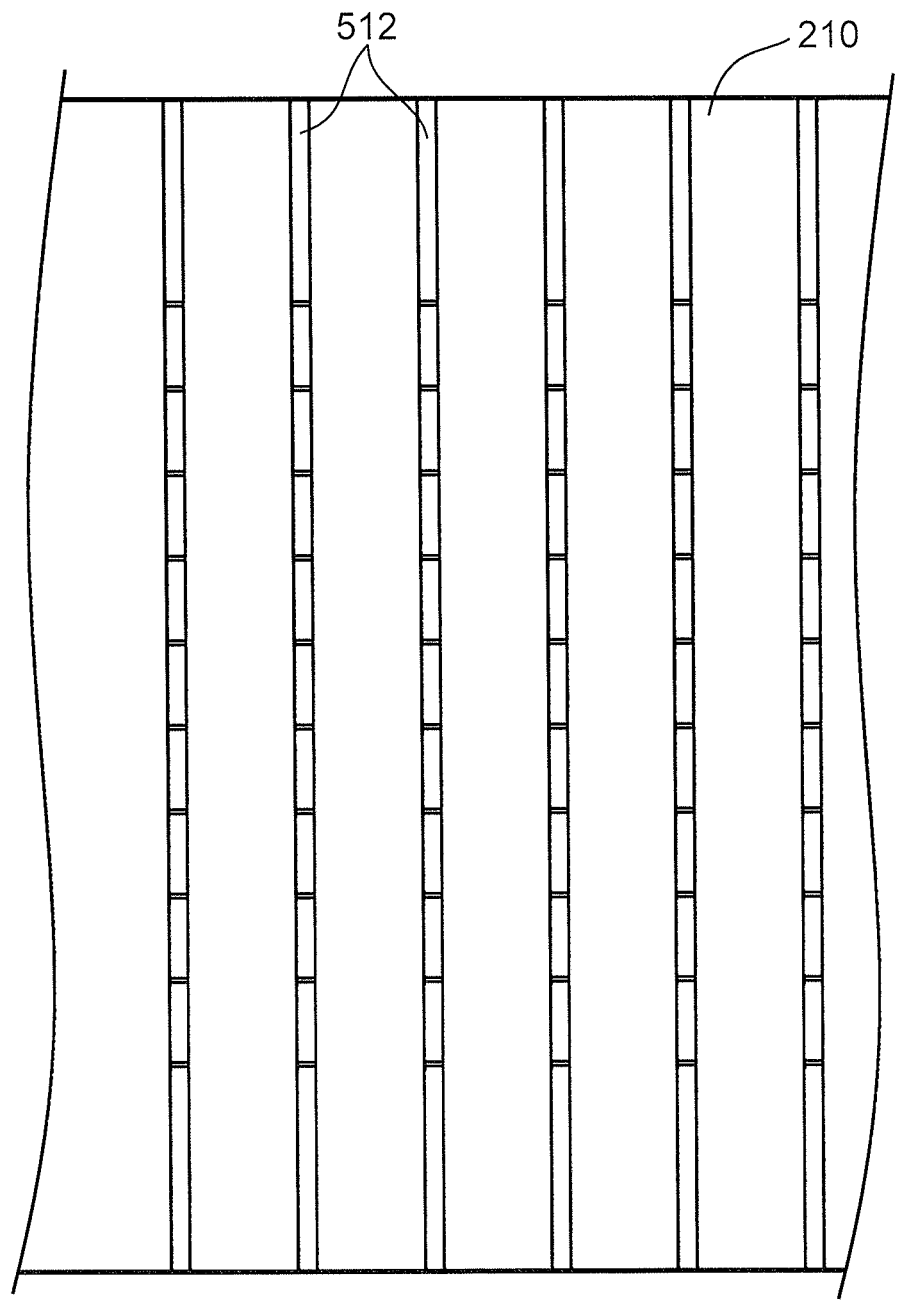
FIG. 17 is a diagram depicting a convex section in another embodiment of the present invention.

Further, one of a group of the first convex sections 212a and a group of the second convex sections 212b may be omitted. In this case, as depicted in FIG. 17, a plurality of convex sections (unit-convex sections) 512 may be formed to extend in a direction orthogonal to the conveyance direction of the anvil roller 210.

Thus, each bonded section formed in each of the sheets 2a, 2b by the convex sections 512 has a shape extending in the width direction of the sheets 2a, 2b (direction orthogonal to the stretchable direction of the composite stretchable member 1), so that it is possible to increase a bonding force between the sheets 2a, 2b, in the width direction.

When the convex sections 512 are arranged in the conveyance direction of the anvil roller 210 in parallel relation to each other, in the above manner, the output portion 221 of the horn 211 will intermittently come into contact with the convex sections 512. This is likely to cause large vibration and noise.

Figure 18:
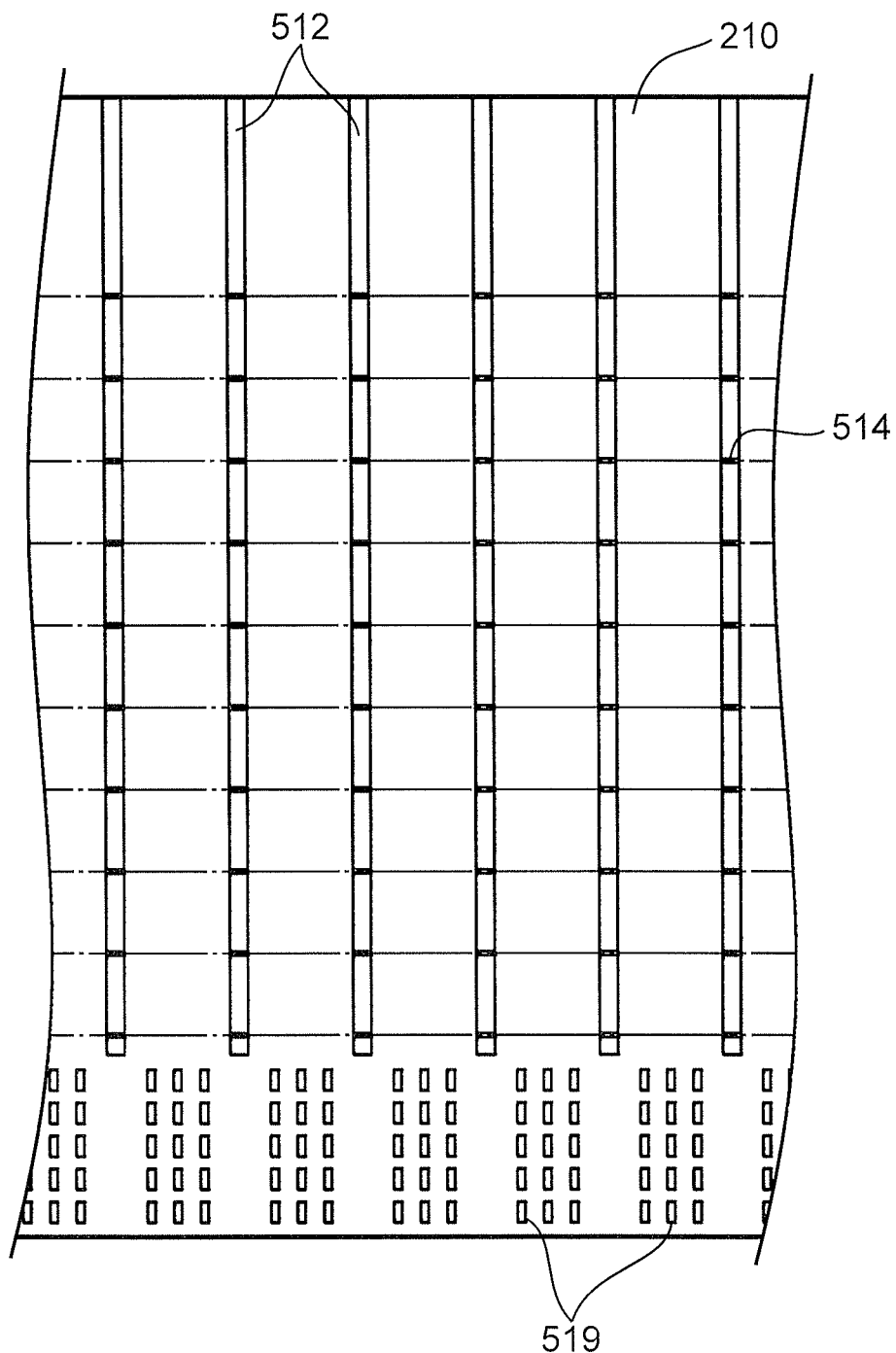
FIG. 18 is a diagram depicting a convex section in yet another embodiment of the present invention.

For this reason, in the case where each of the convex sections 512 is provided in the conveyance direction of the anvil roller 210 in parallel relation to each other, it is preferable to provide an auxiliary convex section 519 in an edge region located in a width direction of the anvil roller 210 (a direction parallel to the rotational axis of the anvil roller 210), as depicted in FIG. 18.

Specifically, in addition to the convex sections 512 for bonding the sheets 2a, 2b together while sandwiching the elastic elements 10 therebetween, an auxiliary convex section 519 for bonding only the sheets 2a, 2b together is provided in an edge region of the outer peripheral surface of the anvil roller 210 in the width direction thereof. Further, the auxiliary convex section 501 is provided between adjacent ones of the convex sections 512 in the conveyance direction of the anvil roller 210.

In the example depicted in FIG. 18, a plurality of (in the example depicted in FIG. 18, five) auxiliary convex sections 519 are provided in spaced-apart relation to each other in the width direction of the anvil roller 210 to form a line, and three lines of the plurality of auxiliary convex sections 519 are provided between adjacent ones of the convex sections 512 in the conveyance direction of the anvil roller 210.

Thus, it becomes possible to enable the output portion 221 of the horn 220 to continuously come into contact with a plurality of convex sections comprising the convex sections 512 and the auxiliary convex sections 519. This makes it possible to keep down noise and vibration which would otherwise occur when the output portion 221 of the horn 220 starts to come into contact with each of the convex sections.

The auxiliary convex section 519 may be formed continuously along the conveyance direction of the anvil roller 210. In this case, it is possible to more reliably enable the output portion 221 of the horn 220 to continuously come into contact with the convex sections. However, the auxiliary convex section 519 has a relatively small dimension in the width direction of the anvil roller 210. Thus, during contact between the auxiliary convex section 519 and the output portion 221 of the horn 220, a relatively large force is applied to a region of the sheets 2a, 2b clamped therebetween, so that the sheets 2a, 2b are likely to undergo breakage. Thus, in the case where the auxiliary convex section 501 is continuously provided along the conveyance direction of the anvil roller 210, as mentioned above, the sheets 2a, 2b are likely to be broken along the auxiliary convex section 519, and divided into a portion in contact with the auxiliary convex section 519 and the remaining portion. Therefore, when there is a risk of breakage of the sheets 2a, 2b, it is preferable to intermittently provide a plurality of auxiliary convex sections 519, as depicted in FIG. 18.

Further, after passing through the anvil roller 210, a region of the bonded sheets 2a, 2b formed by the auxiliary convex sections 519 may be cut off, or may be used as part of the composite stretchable member 501 in a bent state or the like.

Figure 19:
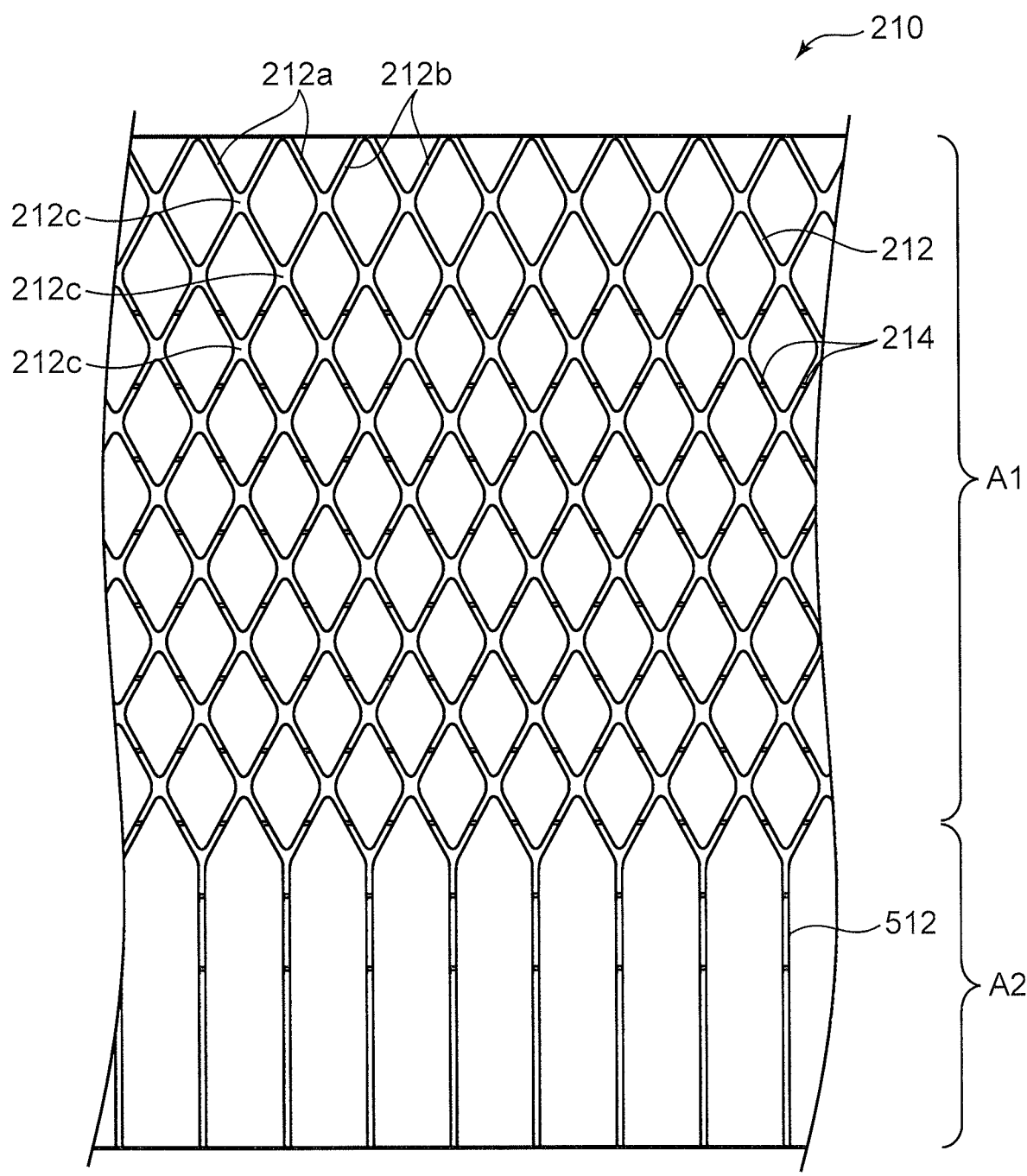
FIG. 19 is a diagram depicting a convex section in still another embodiment of the present invention.

Further, as depicted in FIG. 19, the outer peripheral surface of the anvil roller 210 may be formed to have an intersecting pattern region A1 with a convex section comprising the first convex sections 212a and the second convex sections 212b, and a straight pattern region A2 comprising a plurality of convex sections (third convex sections) 512 each extending in the direction orthogonal to the conveyance direction of the anvil roller 210, as depicted in FIG. 17, wherein each of the convex sections 512 extends from a respective one of part of intersection points of the first convex sections 212a with the second convex sections 212b, in the width direction of the anvil roller 210. This makes it possible to increase a bonding force between the sheets 2a, 2b along the width direction, in the straight pattern region A2, while increasing a bonding force between the sheets 2a, 2b along a direction intersecting the width direction, in the intersecting pattern region A1.

These sheets 2a, 2b may be applied to a waist portion of a wearable article such as the aforementioned disposable diaper 20, wherein the straight pattern region A2 may be disposed in an edge region of the waist portion in such a manner that each of a plurality of bonding sections 504 corresponding to the convex sections 512 extends inwardly from an edge of the waist portion. In this case, gathers formed in the intersecting pattern region A1 can provide good appearance and good feel, and gathers formed in the straight pattern region A2 can form open spaces opened outwardly from the edge of the waist portion to provide good breathability. That is, in the straight pattern region A2, passages providing fluid communication between an inside and an outside of the waist portion are formed between adjacent ones of the bonding sections 504, so that it is possible to provide good breathability.

Figure 20:
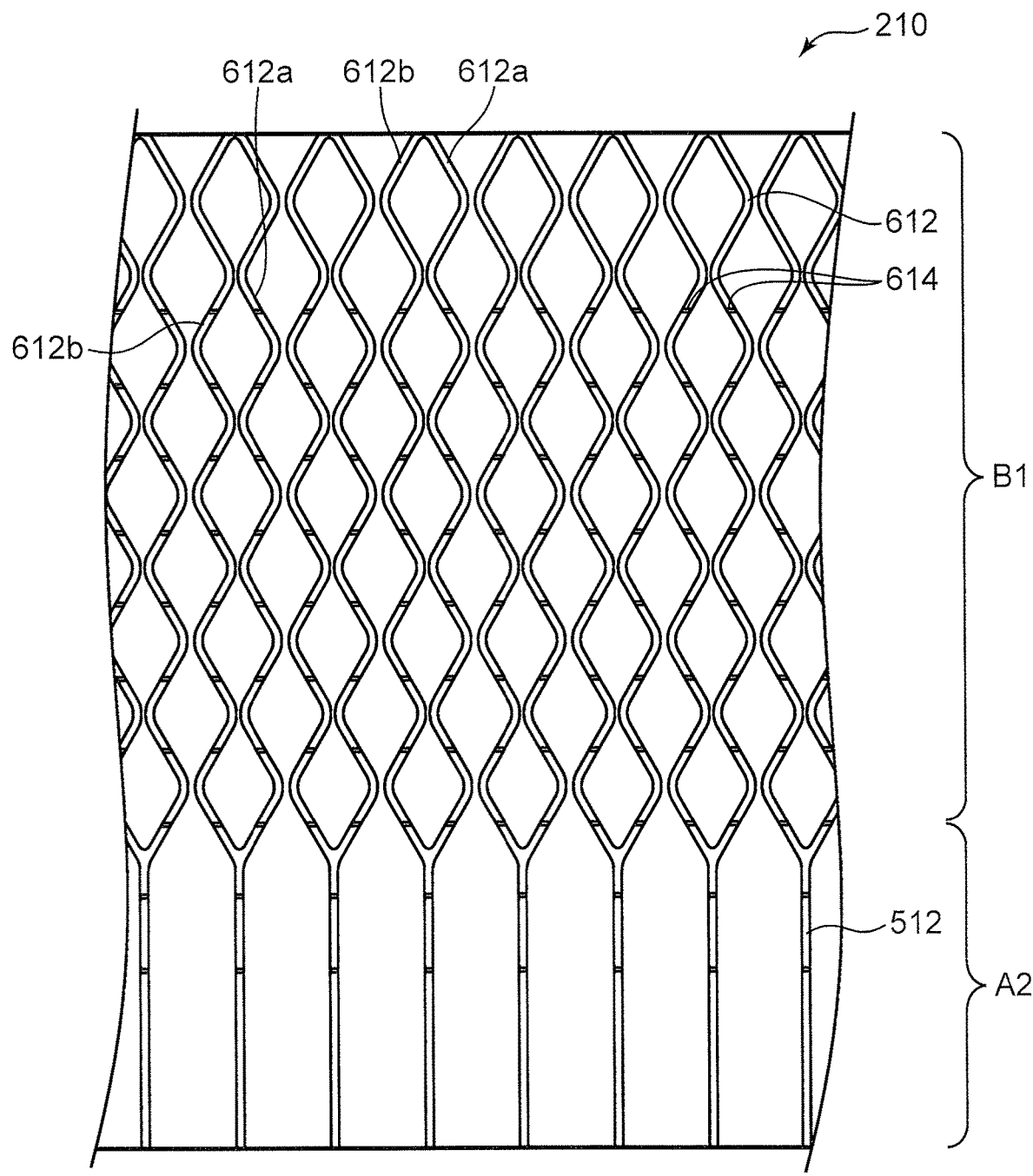
FIG. 20 is a diagram depicting a convex section in yet still another embodiment of the present invention.

Further, the outer peripheral surface of the anvil roller 210 may be formed with a convex section 612 as depicted in FIG. 20.

In the example depicted in FIG. 20, a plurality of convex sections 612 each extending along a zigzag line intersecting the conveyance direction of the anvil roller 210, i.e., a line extending in the width direction of the anvil roller 210, while bending toward one side and the other side of the conveyance direction of the anvil roller 210 plural times, are provided in a region B1 other than the straight pattern region A2, in place of the intersecting pattern region A1 in FIG. 19.

More specifically, in the example depicted in FIG. 20, in the region B1, the convex sections 612 comprise: a plurality of first unit-convex sections 612a lying side-by-side in the conveyance direction of the anvil roller 210 in parallel relation to each other, and a plurality of second unit-convex sections 612b located between adjacent ones of the first unit-convex sections 612a and lying side-by-side in the conveyance direction of the anvil roller 210 in parallel relation to each other. Each of the unit-convex sections 612a, 612b has a shape extending from one edge toward the other edge of the anvil roller in the width direction thereof (direction parallel to the rotational axis of the anvil roller 210), while alternately inclining toward one side and the other side of the conveyance direction of the anvil roller 210. Further, each of the unit-convex sections 612a, 612b has a symmetrical shape with respect to a line extending along the width direction of the anvil roller 210.

In each of the unit-convex sections 612a, 612b, a plurality of grooves 612 are formed, respectively, in central portions between adjacent ones of a plurality of curved portions in each of which an inclination direction changes, to allow each of the elastic elements 10 to be set in a corresponding one thereof. Accordingly, each of the elastic elements 10 is disposed between the sheets 2a, 2b in a posture extending in the conveyance direction along which the sheets 2a, 2b are conveyed.

In a boundary area between the region B1 and the straight pattern region A2, adjacent ones of the first unit-bonding sections 612a and the second unit-bonding sections 612b are joined together, and each of the convex sections 512 forming a straight pattern linearly extends from the joined position along in the width direction of the anvil rollers 210.

When the anvil roller 210 is configured in the above manner, it becomes possible to keep down a ratio per unit area of the bonding sections formed by the convex section to the sheet (2a, 2b), as compared to the anvil roller depicted in FIG. 19. Specifically, in the example depicted in FIG. 19, the first convex sections 212a and the second convex sections 212b intersect each other, so that an area percentage per unit area of the bonding sections 4 becomes larger, in a vicinity of the bonding section 4(4c) formed at the intersection point 212c therebetween. Accordingly, in the vicinity of the intersection point, the composite stretchable member becomes harder. Differently, in the example depicted in FIG. 20, the unit-concave sections 612a, 612b do not intersect each other (except the boundary area between the region B1 and the straight pattern region A2), so that it becomes possible to suppress an increase in area of bonding sections 4 to be formed (area percentage per unit area of the bonding sections) so as to suppress hardening of the composite stretchable member and provide good feel.

Spaced-apart distances between adjacent ones of the elastic elements 10 need not necessarily be identical to each other, and spaced-apart distances between adjacent ones of the grooves 214 need not necessarily be constant. The elastic elements 10 may be arranged in non-parallel relation to extend in directions causing them to intersect each other, and the grooves 214 may be arranged to extend in directions causing them to intersect each other, instead of extending along the circumferential direction of the anvil roller 210.

Further, one of the group of first convex sections 212a and the group of the second convex sections 212b may be formed in a shape extending in the direction orthogonal to the circumferential direction of the anvil roller 210, to allow one of the group of first bonding sections 4a and the group of second bonding sections 4b to extend in the direction orthogonal to the longitudinal direction of the sheets 2a, 2b.

Alternatively, one or each of the group of first convex sections 212a and the group of second convex sections 212b may be arranged to incline at an angle of 45 degree or more, with respect to the direction orthogonal to the conveyance direction of the anvil roller 210, to allow one or each of the group of first bonding sections 4a and the group of second bonding sections 4b to incline at an angle of 45 degree or more, with respect to the width direction of the sheets 2a, 2b (the direction orthogonal to the stretchable direction of the composite stretchable member 1).

Further, the intersection points 212c of the first convex sections 212a with the second convex sections 212b need not necessarily be arranged to lie in a straight line extending in the direction orthogonal to the conveyance direction of the anvil roller 210. That is, the intersection points 212c may be offset from each other in the conveyance direction of the anvil roller 210. Then, the intersection points 4c of the first bonding sections 4a with the second bonding sections 4b may be formed such that they are offset from each other in the longitudinal direction of the sheets 2a, 2b.

Further, the grooves 214 may be formed, respectively, at the intersection points 212c of the first convex sections 212a with the second convex sections 212b. Then, each of the elastic elements 10 may be disposed to pass through two or more of the intersection points of the first bonding sections 4a with the second bonding sections 4b (the bonding section-side intersection points 4c), and bonded to the sheets 2a, 2b at the points.

Further, the grooves 214a formed on each of the first convex sections 212a and the grooves 214b formed on each of the second convex sections 212b may be arranged in offset relation to each other with respect to a straight line extending in the direction orthogonal to the conveyance direction of the anvil roller 210. That is, positions of the grooves 214a, 214b in the conveyance direction of the anvil roller 210 may be offset from each other. Then, positions of the intersection points 4d of the elastic elements 10 with the first bonding sections 4a, and positions of the intersection points 4e of the elastic elements 10 with the second bonding sections 4b, may be offset from each other with respect to the longitudinal direction of the sheets 2a, 2b.

Further, the grooves 214 may be arranged at unequal intervals in the conveyance direction of the anvil roller 210. Then, the intersection points 4d, 4e of the elastic elements 10 with the bonding sections 4 may be formed at unequal intervals in the longitudinal direction of the sheets 2a, 2b.

The bonded structure of the elastic elements 10 and the sheets 2a, 2b are not limited to the above. That is, the rubber strings 10a in the elastic elements 10 may be bonded to the sheets 2a, 2b. For example, each of the elastic elements 10 may comprise a plurality of rubber strings 10a assembled as a bundle, wherein the sheets 2a, 2b may be welded to at least one of the rubber strings 10a located in an outer periphery of the elastic element 10. Even in this case, the sheets 2a, 2b are welded to the rubber strings 10a located in the outer periphery of the elastic element 10, so that it is possible to suppress damage to the remaining, non-bonded rubber strings 10a.

Further, each of the elastic elements 10 may be formed using silicone oil having a relatively low boiling point or the like, as the covering layer 10b. In this case, during welding of the elastic element 10 to the sheets 2a, 2b, after vaporizing the covering layer 10b, part of the rubber strings 10a may be directly bonded to the sheets 2a, 2b. In this case, as the rubber strings 10a, rubber strings having an adhesive force (cohesion) may be employed. Then, the rubber strings 10a may be bonded to the sheets 2a, 2b by means of the adhesive force.

Further, the production method for the disposable diaper 20 using the composite stretchable member 1 is not limited to the above.

Figure 21:
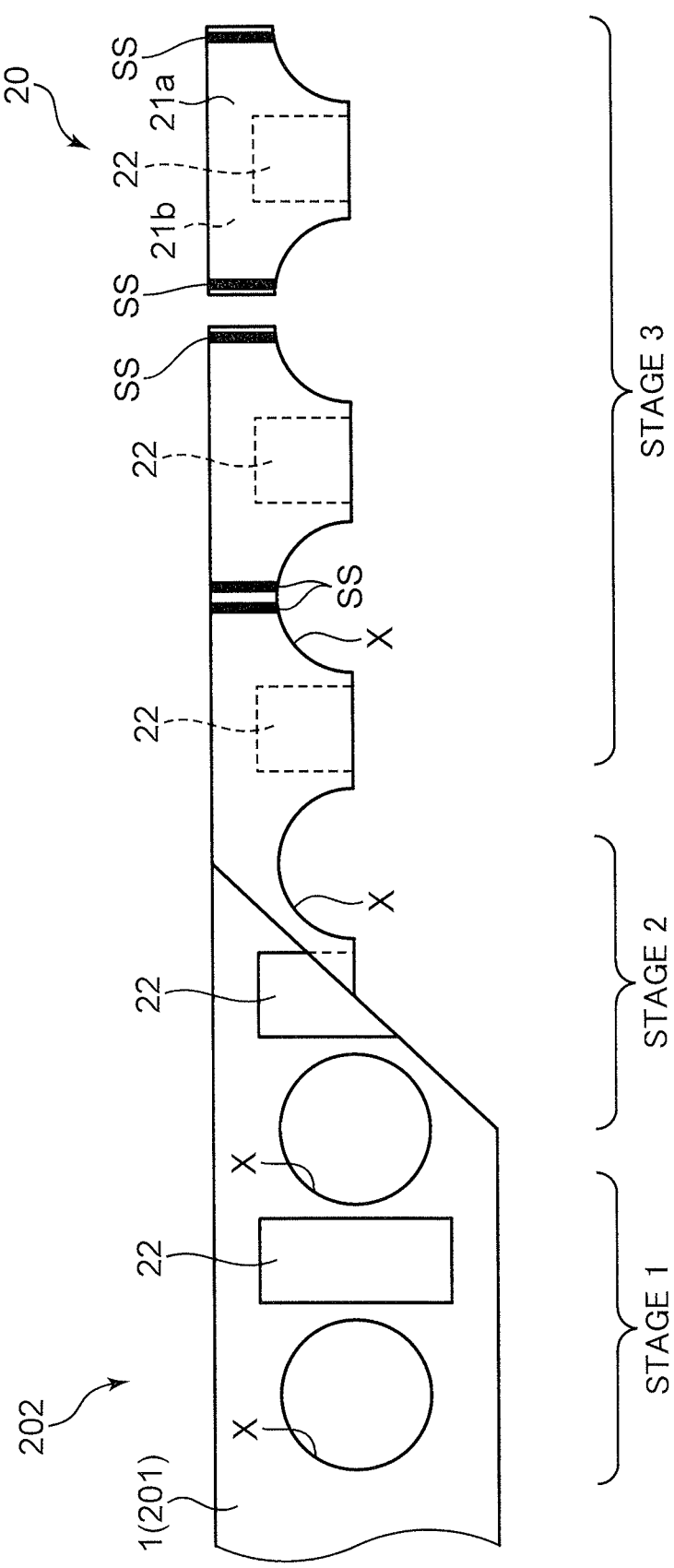
FIG. 21 is a diagram for explaining another example of the production method for the disposable diaper depicted in FIG. 15.

For example, the disposable diaper 20 may be produced in a process as depicted in FIG. 21.

Specifically, in this method, in a stage 1, one continuous body 201 of the composite stretchable member 1 extending in a conveyance direction is prepared, and conveyed in a longitudinal direction thereof. Further, a plurality of crotch portions 22 are arranged in a widthwise central region of the continuous body 201, in such a manner that a longitudinal direction of each of the crotch portions 22 is oriented orthogonal to the longitudinal direction of the continuous body 201. Then, the crotch portions 22 and the continuous body 201 are bonded together to form a bonded body 202 (bonded body forming step). In this method, a plurality of pairs of holes X each serving as leg openings for allowing legs of a wearer to be inserted therethrough are preliminarily formed in the continuous body 201, and then the crotch portions 22 are bonded to the continuous body 201. The formation of the holes X may be performed after bonding the crotch portions 22 to the continuous body 201.

Subsequently, in a stage 2, the bonded body 102 is double-folded along a folding line defined by a center line of the bonded body 102 in a width direction (a direction orthogonal to the longitudinal direction of the continuous body), in such a manner that each of the crotch portions 22 is located inward of the continuous body (double-folding step).

A stage 3 is the same as that in the above embodiment. That is, in the stage 3, superimposed portions of the continuous body 201 at an intermediate position between adjacent ones of the crotch portions 22 are bonded together along a direction orthogonal to the longitudinal direction of the continuous body 201, to thereby form a side seal (side sealing step), and the continuous body 201 is cut along a cutting line K in the side seal (cutting step).

As with the method in the above embodiment, this method makes it possible to produce a disposable diaper 20 capable of increasing a bonding force in a waist portion 20 thereof to suppressing breakage such as drop-off of the elastic elements 10.

In this method, there is no need to prepare and convey a plurality of continuous bodies of the composite stretchable member 1, so that it is possible to simplify a production apparatus. On the other hand, in the case where the disposable diaper 20 is produced using the pair of continuous bodies of the composite stretchable member 1 as in the above embodiment, it is possible to omit the formation of the holes serving as leg openings.

Although the above embodiment has been described based on an example where the bonding device is a device configured to perform ultrasonic welding, more specifically to give ultrasonic vibration to the sheets 2a, 2b to generate frictional heat to thereby heat the sheets 2a, 2b, a specific configuration for heating and welding the sheets 2a, 2b is not limited thereto. For example, a device capable of heating and welding the sheets 2a, 2b without vibrating the sheets 2a, 2b may be used as the bonding device, and, in the bonding step, the sheets 2a, 2b may be heated and welded without being vibrated, like so-called "heat sealing".

The aforementioned specific embodiments primarily include inventions having the following features.

The present invention provides a composite stretchable member production apparatus for producing a composite stretchable member comprising two sheets and a plurality of elastic elements sandwiched between the two sheets, by bonding the two sheets together and further bonding each of the elastic elements to the sheets, while conveying the two sheets along a longitudinal direction thereof. The composite stretchable member production apparatus comprises: a bonding device which bonds each of the elastic elements to the sheets and further bonds the sheets together, by means of welding, in a state in which the elastic elements are sandwiched between the two sheets being conveyed; and a guide device which guides, to the bonding device, the two sheets and the elastic elements in such a manner as to enable each of the elastic elements to be sandwiched between the two sheets while extending in the longitudinal direction of the sheets, wherein the bonding device comprises: a conveyance roller having an outer peripheral surface rotatable about a given axis to convey the two sheets with the elastic elements sandwiched therebetween, in the longitudinal direction of the sheets; and a clamping and pressing device which is opposed to the outer peripheral surface of the conveyance roller, and clamps and presses the two sheets with the elastic elements sandwiched therebetween, in cooperation with the outer peripheral surface, wherein the bonding device is configured to apply heat to the sheets between the conveyance roller and the clamping and pressing device, and wherein the outer peripheral surface of the conveyance roller is formed with at least one convex section protruding toward the clamping and pressing device, wherein the convex section has a shape extending along a line intersecting a conveyance direction of the conveyance roller, and has a plurality of grooves lying in spaced-apart relation to each other on the line intersecting the conveyance direction of the conveyance roller and each extending in the conveyance direction of the conveyance roller.

In this apparatus, the sheets and the elastic elements are heated and pressed to weld the sheets together and further weld each of the elastic elements to the sheets, so that, as compared to the case where the bonding is performed using a hot-melt material, it becomes unnecessary to prepare the hot-melt material. Further, it is possible to bond together the two sheets with the elastic elements therebetween, while conveying the two sheets by the conveyance roller, so that, as compared to the case where a device for applying a hot-melt material is provided, it becomes possible to simplify production equipment to suppress power consumption.

On the other hand, in this apparatus, it is necessary to clamp and press the two sheets with the elastic elements sandwiched therebetween, so that there is a possibility that the elastic elements are damaged by the pressing. Considering this, in this apparatus, the convex section formed on the outer peripheral surface of the conveyance roller is formed with the grooves each extending in the conveyance direction of the conveyance roller. Thus, when the sheets are clamped and pressed by the convex section and the clamping and pressing) device, the elastic elements are allowed to escape into the grooves. This makes it possible to keep down a pressure to be applied to the elastic elements to thereby suppress damage to the elastic elements.

Further, in this apparatus, the convex section extends in a direction intersecting the conveyance direction of the conveyance roller, and the plurality of grooves are provided on the convex section at positions spaced apart from each other on the line intersecting the conveyance direction of the conveyance roller. Thus, it is possible to bond the sheets together and further bond each of the elastic elements to the sheets in the conveyance direction along which the two sheets are conveyed, while allowing the elastic elements to escape into the grooves.

Preferably, in the above production apparatus, a cross-sectional shape of each of the grooves taken along a plane orthogonal to the conveyance direction of the conveyance roller is set such that, when the elastic element is disposed in one of the grooves in a state in which the elastic element has a natural length, a part of the elastic element disposed in the groove protrudes outwardly in a radial direction of the conveyance roller with respect to a linear imaginary line connecting opening edges of the groove.

According to this feature, during bonding, it is possible to moderately press each of the elastic elements disposed in a corresponding one of the grooves, and the sheets, to bond them together, while allowing the elastic element to escape into the groove, so that it becomes possible to more reliably bond each of the elastic elements to the sheets while suppressing damage to the elastic elements. That is, it is possible to reduce a pressure to be applied to a portion of each of the elastic elements received inside a corresponding one of the grooves, while appropriately pressing the remaining portion of the elastic element protruding outwardly with respect to an imaginary line connecting opening edges of the groove, thereby suppressing damage to the elastic elements while ensuring a bonding force.

Preferably, in the production apparatus of the present invention, a cross-sectional shape of each of the grooves taken along a plane orthogonal to the conveyance direction of the conveyance roller is set such that, when the elastic element is disposed in one of the grooves in a state in which the elastic element is stretched three times a natural length thereof, a part of the elastic element disposed in the groove protrudes outwardly in a radial direction of the conveyance roller with respect to a linear imaginary line connecting opening edges of the groove.

According to this feature, it becomes possible to more reliably bond each of the elastic elements to the sheets while suppressing damage to the elastic elements.

Preferably, in the production apparatus of the present invention, each of the elastic elements comprises a plurality of fiber-shaped elastic bodies assembled as a bundle, wherein peripheral surfaces of at least part of the plurality of fiber-shaped elastic bodies are covered, respectively, by covering layers, and the bonding device is operable to cause the covering layers to be melted and welded to the sheets.

According to this feature, it becomes possible to more effectively suppress damage to the elastic bodies or the like which would otherwise occur when the fiber-shaped elastic bodies are clamped and pressed during bonding.

Alternatively, each of the elastic elements may comprise a plurality of fiber-shaped elastic bodies assembled as a bundle, wherein each of the sheets may be welded to at least one of the fiber-shaped elastic bodies located in a periphery of the elastic element, whereby the elastic element and the sheet are bonded together.

In this case, it also becomes possible to more effectively suppress damage to the elastic bodies or the like which would otherwise occur when the fiber-shaped elastic bodies are clamped and pressed during bonding.

Preferably, in the production apparatus of the present invention, the guide device comprises a guide member having a distal edge opposed to the outer peripheral surface of the conveyance roller, and a base edge disposed farther away from the conveyance roller than the distal edge, wherein the guide member is configured to guide the plurality of elastic elements to the outer peripheral surface of the conveyance roller, in a state where the plurality of elastic elements 10 are spaced apart from each other in a direction parallel to the axis of the conveyance roller, and wherein the distal edge of the guide member is formed with a plurality of notches each for holding a respective one of the elastic elements, at positions spaced apart from each other in a direction parallel to the axis of the conveyance roller.

According to this feature, it becomes possible to guide the elastic elements to the conveyance roller, at more appropriate positions. In particularly, it is possible to more reliably set the elastic elements, respectively, in the grooves, thereby suppressing damage to the elastic elements.

Preferably, in the production apparatus of the present invention, the convex section comprises a plurality of unit-convex sections each extending in a direction orthogonal to the conveyance direction of the conveyance roller.

According to this feature, the bonding section in which the two sheets are bonded together can be formed in a shape extending in a direction orthogonal to a stretchable direction of the composite stretchable member, so that it becomes possible to increase a bonding force between the sheets in the stretchable direction.

Alternatively, the convex section may comprise: a plurality of first convex sections extending parallel to each other along a first direction intersecting the conveyance direction of the conveyance roller; and a plurality of second convex sections extending parallel to each other along a second direction intersecting the conveyance direction of the conveyance roller and the first direction, and each intersecting at least one of the first convex sections.

According to this feature, the sheets can be bonded together on lines extending in different directions. Thus, even in a situation where an external force is applied to the composite stretchable member from various directions, it is possible to more reliably suppress debonding between the sheets or between associated ones of the sheets and the elastic elements. Further, bonding sections formed in each of the sheets by the first convex sections and bonding sections formed in each of the sheets by the second convex sections intersect each other, so that it is possible to increase a bonding force between the sheets in the vicinity of each of the intersection points, and thus increase a bonding force in the entire composite stretchable member.

Preferably, in the above production apparatus, each of the first direction and the second direction is a direction intersecting a direction orthogonal to the conveyance direction of the conveyance roller.

According to this feature, when an external force is applied to the bonding sections formed in each of the sheets by the first convex sections and the bonding sections formed in each of the sheets by the second convex sections 4b, during use of the composite stretchable member, it is possible to reduce a normal component of the external force with respect to each of the bonding sections, and more reliably suppress debonding between the sheets in the bonding sections.

Preferably, in the above production apparatus, each of the first direction and the second direction is inclined at an angle of less than 45 degrees, with respect to the direction orthogonal to the conveyance direction of the conveyance roller.

According to this feature, it is possible to reduce a distance between the intersection points of each of the elastic elements with the bonding sections in the longitudinal direction of the sheets. This makes it possible to more finely form gathers between bonded points in the stretchable direction of the composite stretchable member, in a non-stretched state of the composite stretchable member. Therefore, it is possible to provide a better feel.

Preferably, in the above production apparatus, intersection points of the first convex sections with the second convex sections lie in a line extending in the conveyance direction of the conveyance roller, and lie in a straight line extending in the direction orthogonal to the conveyance direction of the conveyance roller.

According to this feature, the intersection points of the bonding sections formed in each of the sheets by the first convex sections and the bonding sections formed in each of the sheets by the second convex sections 4b can be arranged in an orderly manner, so that it is possible to form gathers between adjacent ones of the intersection points of these bonding sections in a regular pattern. This makes it possible to provide good appearance of the composite stretchable member, and increase a bonding force between the sheets in the longitudinal direction of the sheets and a direction orthogonal to the longitudinal direction.

Preferably, in the above production apparatus, the grooves are formed in regions of the first and second convex sections other than the intersection points of the first convex sections with the second convex sections.

According to this feature, it becomes possible to increase the number of bonded points of each of the elastic elements to the sheets to thereby increase a bonding force between associated ones of the elastic elements and the sheets.

Preferably, in the above production apparatus, first grooves formed on the first convex sections, and second grooves formed on the second convex sections, lie in a straight line extending in a direction orthogonal to the conveyance direction of the conveyance roller.

According to this feature, it is possible to form gathers between adjacent ones of the bonded points of each of the elastic elements to the sheets, in such a manner as to lie in a straight line extending in the width direction of the sheets, thereby providing good appearance of the composite stretchable member.

Preferably, in the above production apparatus, the grooves are formed in regions of the first and second convex sections other than the intersection points of the first convex sections with the second convex sections, and provided at equal intervals in the conveyance direction of the conveyance roller.

According to this feature, sizes of gathers formed between adjacent ones of the bonded points of each of the elastic elements to the sheets (dimensions of the gathers protruding outwardly can be uniformed in the longitudinal direction of the sheets, while increasing a bonding force between the sheets and a bonding force between each of the elastic elements to the sheets. This makes it possible to provide good appearance and good feel of the composite stretchable member.

Preferably, in the above production apparatus, the outer peripheral surface of the conveyance roller includes: an intersecting pattern region in which the convex sections comprise the plurality of first convex sections and the plurality of second convex sections; and a straight pattern region which is located next to the intersecting pattern region and in which the convex sections comprise a plurality of third convex sections each extending from a respective one of part of intersection points of the first convex sections with the second convex sections, in a direction orthogonal to the conveyance direction of the conveyance roller.

According to this feature, it becomes possible to further increase a bonding force between the sheets in a direction intersecting the conveyance direction of the conveyance roller, in the intersecting pattern region, and increase a bonding force between the sheets in the conveyance direction of the conveyance roller, in the straight pattern region. In the case where the composite stretchable member is applied to a waist portion of a wearable article, gathers formed in the intersecting pattern region can provide good appearance and good feel, and gathers formed in the straight pattern region can form open spaces opened outwardly from an edge of the waist portion to provide good breathability.

The present invention also provides a composite stretchable member production method for producing a composite stretchable member using the above composite stretchable member production apparatus. The composite stretchable member production method comprises: a guiding step of guiding, to the bonding device by the guide device, two sheets and a plurality of elastic elements in such a manner to each of the elastic elements to be sandwiched between the two sheets while extending in a longitudinal direction of the sheets; and a bonding step of clamping and pressing, by the clamping and pressing device and the convex section, the two sheets with the elastic elements sandwiched therebetween, and heating a clamped and pressed part of the two sheets to thereby bond each of the elastic elements to the sheets and further bond the sheets together, by means of welding, wherein the bonding step includes bonding each of the elastic elements to the sheets and further bonding the sheets together, in a state in which each of the elastic elements is disposed on a portion of one of the sheet located on the side of the conveyance roller, and part of the portion of the sheet and at least part of the elastic element are inserted in ones of the grooves of the convex section.

The production method of the present invention makes it possible to produce a composite stretchable member configured to be appropriately stretched and restored by a plurality of elastic elements, using a production apparatus capable of ensuring a bonding force between two sheets and a bonding force between associated ones of the elastic elements and the sheets, while suppressing damage to the elastic elements, as mentioned above.

The invention claimed is:

1. A composite stretchable member production apparatus for producing a composite stretchable member comprising two sheets and a plurality of elastic elements sandwiched between the two sheets, by bonding the two sheets together and further bonding each of the elastic elements to the sheets, while conveying the two sheets along a longitudinal direction thereof, the composite stretchable member production apparatus comprising:

a bonding device configured to bond each of the elastic elements to the sheets and further bond the sheets together, by welding, in a state in which the elastic elements are sandwiched between the two sheets being conveyed; and a guide device configured to guide, to the bonding device, the two sheets and the elastic elements so as to enable each of the elastic elements to be sandwiched between the two sheets while extending in the longitudinal direction of the sheets, wherein the bonding device comprises: a conveyance roller having an outer peripheral surface rotatable about an axis to convey the two sheets with the elastic elements sandwiched therebetween, in the longitudinal direction of the sheets; and a clamping and pressing device which is opposed to the outer peripheral surface of the conveyance roller, and configured to clamp and press the two sheets with the elastic elements sandwiched therebetween, in cooperation with the outer peripheral surface of the conveyance roller, the bonding device being configured to apply heat to the sheets between the conveyance roller and the clamping and pressing device, wherein the outer peripheral surface of the conveyance roller is formed with at least one convex section protruding toward the clamping and pressing device, the at least one convex section having a shape continuously extending along a line intersecting a conveyance direction of the conveyance roller, and having a plurality of grooves lying in spaced-apart relation to each other on the line intersecting the conveyance direction of the conveyance roller and each extending in the conveyance direction of the conveyance roller, wherein the guide device comprises a guide member having a distal edge opposed to the outer peripheral surface of the conveyance roller, and a base edge disposed farther away from the conveyance roller than the distal edge, the guide member being configured to guide each of the elastic elements to each of the grooves, in a state where the elastic elements are spaced apart from each other in a direction parallel to the axis of the conveyance roller, wherein the guide member is formed in a shape tapered toward the distal edge, and wherein the distal edge of the guide member is formed with a plurality of notches each for holding a respective one of the elastic elements, at positions spaced apart from each other at same intervals as the grooves in the direction parallel to the axis of the conveyance roller, and in opposed relation to each of the grooves.

2. The composite stretchable member production apparatus according to claim 1, wherein a cross-sectional shape of each of the grooves taken along a plane orthogonal to the conveyance direction of the conveyance roller is set such that, when one of the elastic elements is disposed in one of the grooves in a state in which the one of the elastic elements has a natural length, a part of the one of the elastic elements disposed in the one of the grooves protrudes outwardly in a radial direction of the conveyance roller with respect to a linear imaginary line connecting opening edges of the one of the grooves.

3. The composite stretchable member production apparatus according to claim 1, wherein a cross-sectional shape of each of the grooves taken along a plane orthogonal to the conveyance direction of the conveyance roller is set such that, when one of the elastic elements is disposed in one of the grooves in a state in which the one of the elastic elements is stretched three times a natural length thereof, a part of the one of the elastic elements disposed in the one of the grooves protrudes outwardly in a radial direction of the conveyance roller with respect to a linear imaginary line connecting opening edges of the one of the grooves.

4. The composite stretchable member production apparatus according to claim 1, wherein each of the elastic elements comprises a plurality of fiber-shaped elastic bodies assembled as a bundle, and wherein peripheral surfaces of at least part of the plurality of fiber-shaped elastic bodies are covered, respectively, by covering layers, and the bonding device is operable to cause the covering layers to be melted and welded to the sheets.

5. The composite stretchable member production apparatus according to claim 1, wherein each of the elastic elements comprises a plurality of fiber-shaped elastic bodies assembled as a bundle, and wherein each of the sheets is welded to at least one of the fiber-shaped elastic bodies located in a periphery of each of the elastic elements, whereby each of the elastic elements and each of the sheets are bonded together.

6. The composite stretchable member production apparatus according to claim 1, wherein the at least one convex section comprises a plurality of unit-convex sections each extending in a direction orthogonal to the conveyance direction of the conveyance roller.

7. The composite stretchable member production apparatus according to claim 1, wherein the at least one convex section comprises:

a plurality of first convex sections extending parallel to each other along a first direction intersecting the conveyance direction of the conveyance roller; and a plurality of second convex sections extending parallel to each other along a second direction intersecting the conveyance direction of the conveyance roller and the first direction, and each intersecting at least one of the first convex sections.

8. The composite stretchable member production apparatus according to claim 7, wherein each of the first direction and the second direction intersects a direction orthogonal to the conveyance direction of the conveyance roller.

9. The composite stretchable member production apparatus according to claim 8, wherein each of the first direction and the second direction is inclined at an angle of less than 45 degrees, with respect to the direction orthogonal to the conveyance direction of the conveyance roller.

10. The composite stretchable member production apparatus according to claim 8, wherein intersection points of the first convex sections with the second convex sections lie in a line extending in the conveyance direction of the conveyance roller, and lie in a straight line extending in the direction orthogonal to the conveyance direction of the conveyance roller.

11. The composite stretchable member production apparatus according to claim 7, wherein the grooves are formed in regions of the first convex sections and the second convex sections other than intersection points of the first convex sections with the second convex sections.

12. The composite stretchable member production apparatus according to claim 7, wherein first grooves formed on the first convex sections, and second grooves formed on the second convex sections, lie in a straight line extending in a direction orthogonal to the conveyance direction of the conveyance roller.

13. The composite stretchable member production apparatus according to claim 10, wherein the grooves are formed in regions of the first convex sections and the second convex sections other than the intersection points of the first convex sections with the second convex sections, and provided at equal intervals in the conveyance direction of the conveyance roller.

14. The composite stretchable member production apparatus according to claim 7, wherein the outer peripheral surface of the conveyance roller includes:
   an intersecting pattern region in which the at least one convex section comprises the plurality of first convex sections and the plurality of second convex sections; and
   a straight pattern region which is located next to the intersecting pattern region and in which the at least one convex section comprises a plurality of third convex sections each extending from a respective one of part of intersection points of the first convex sections with the second convex sections, in a direction orthogonal to the conveyance direction of the conveyance roller.

15. A composite stretchable member production method for producing a composite stretchable member using the composite stretchable member production apparatus according to claim 1, the composite stretchable member production method comprising:
   a guiding step of guiding, to the bonding device by the guide device, two sheets and a plurality of elastic elements so as to enable each of the elastic elements to be sandwiched between the two sheets while extending in a longitudinal direction of the sheets; and
   a bonding step of clamping and pressing, by the clamping and pressing device and the at least one convex section, the two sheets with the elastic elements sandwiched therebetween, and heating a clamped and pressed part of the two sheets to thereby bond each of the elastic elements to the sheets and further bond the sheets together, by welding,
   wherein the bonding step includes bonding each of the elastic elements to the sheets and further bonding the sheets together, in a state in which each of the elastic elements is disposed on a portion of one of the sheets located on a side of the conveyance roller, and part of the portion of the one of the sheets and at least part of one of the elastic elements are inserted in one of the grooves of the at least one convex section.

16. A composite stretchable member production apparatus for producing a composite stretchable member comprising two sheets and a plurality of elastic elements sandwiched between the two sheets, by bonding the two sheets together and further bonding each of the elastic elements to the sheets, while conveying the two sheets along a longitudinal direction thereof, the composite stretchable member production apparatus comprising:
   a bonding device configured to bond each of the elastic elements to the sheets and further bond the sheets together, by welding, in a state in which the elastic elements are sandwiched between the two sheets being conveyed; and
   a guide device configured to guide, to the bonding device, the two sheets and the elastic elements so as to enable each of the elastic elements to be sandwiched between the two sheets while extending in the longitudinal direction of the sheets,
   wherein the bonding device comprises: a conveyance roller having an outer peripheral surface rotatable about an axis to convey the two sheets with the elastic elements sandwiched therebetween, in the longitudinal direction of the sheets; and a clamping and pressing device which is opposed to the outer peripheral surface of the conveyance roller, and configured to clamp and press the two sheets with the elastic elements sandwiched therebetween, in cooperation with the outer peripheral surface of the conveyance roller, the bonding device being configured to apply heat to the sheets between the conveyance roller and the clamping and pressing device,
   wherein the outer peripheral surface of the conveyance roller is formed with at least one convex section protruding toward the clamping and pressing device, the at least one convex section having a shape extending along a line intersecting a conveyance direction of the conveyance roller, and having a plurality of grooves lying in spaced-apart relation to each other on the line intersecting the conveyance direction of the conveyance roller and each extending in the conveyance direction of the conveyance roller,
   wherein the at least one convex section comprises a plurality of first convex sections extending parallel to each other along a first direction intersecting the conveyance direction of the conveyance roller and a plurality of second convex sections extending parallel to each other along a second direction intersecting the conveyance direction of the conveyance roller and the first direction, and each intersecting at least one of the first convex sections, and
   wherein the outer peripheral surface of the conveyance roller includes an intersecting pattern region in which the at least one convex section comprises the plurality of first convex sections and the plurality of second convex sections, and a straight pattern region which is located next to the intersecting pattern region and in which the at least one convex section comprises a plurality of third convex sections each extending from a respective one of part of intersection points of the first convex sections with the second convex sections, in a direction orthogonal to the conveyance direction of the conveyance roller.

* * * * *